US008492574B2

(12) United States Patent
Charette et al.

(10) Patent No.: US 8,492,574 B2
(45) Date of Patent: Jul. 23, 2013

(54) METHODS FOR PREPARING DIORANOZINC COMPOUNDS

(76) Inventors: Andre Charette, Longueuil (CA); Alexandre Cote, Princeton, NJ (US); Alexandre Lemire, Montreal (CA)

(*) Notice: Subject to any disclaimer, the term of this patent is extended or adjusted under 35 U.S.C. 154(b) by 555 days.

(21) Appl. No.: 12/591,108

(22) Filed: Nov. 9, 2009

(65) Prior Publication Data
US 2010/0121089 A1     May 13, 2010

Related U.S. Application Data

(63) Continuation-in-part of application No. PCT/CA2008/000864, filed on May 6, 2008.

(60) Provisional application No. 60/916,419, filed on May 7, 2007.

(51) Int. Cl.
*C07F 3/06*     (2006.01)
(52) U.S. Cl.
USPC ............................ 556/129; 556/118; 556/121
(58) Field of Classification Search
USPC ......................... 556/118, 121, 129
See application file for complete search history.

(56) References Cited

U.S. PATENT DOCUMENTS

| | | | | | |
|---|---|---|---|---|---|
| 3,663,584 | A | * | 5/1972 | Alvarez | 556/121 |
| 3,975,432 | A | * | 8/1976 | Alvarez | 562/466 |
| 4,812,586 | A | * | 3/1989 | Mullin et al. | 556/129 |
| 5,073,659 | A | * | 12/1991 | Hamamura et al. | 585/600 |
| 5,977,372 | A | * | 11/1999 | Giguere et al. | 548/103 |

FOREIGN PATENT DOCUMENTS
WO         9828306        7/1998

OTHER PUBLICATIONS

Knochel et al., "Preparation and Reactions of Polyfunctional Organozinc Reagents in Organic Synthesis", Chem. Rev. 1993, 93, 2117-2188.
Knochel et al. "Preparation and Applications of Functionalized Organozinc Compounds", Book—Organic Reactions, vol. 58, 2001, pp. 417-730.
Knochel et al., "Polyfunctional Zinc Organometallics for Organic Synthesis", Book—Organometallics, 2005, pp. 251-340.
Knochel et al., "Functionalized Organozinc Compounds", Book—The Chemistry of Organozinc Compounds, 2006, pp. 287-393.
Krasovskiy et la., "Convenient Titration Method for Organometallic Zinc, Magnesium, and Lanthanide Reagents", Synthesis 2006, No. 5, pp. 0890-0891.
Li et al., "Asymmetric Conjugate Addition to α-Halo Enones: Dramatic Effect of Styrene on the Enantioselectivity", Angew. Chem. Int. Ed. 2006, 45, 7600-7603.
Li et al., "Asymmetric Conjugate Addition to α-Halo Enones: Dramatic Effect of Styrene on the Enantioselectivity", Angew. Chem. 2006, 118, 7762-7765.

Lipshutz et al., "Michael Additions of Functionalized Organozinc reagents Mediated by Catalytic Quantities of Copper (I)", J. Am. Chem Soc. 1995, 117, 6126-6127.
Lipshutz et al., "Cu(I)-Catalyzed Substitution Reactions of Activated Vinyl Triflates with Functionalized Organozinc Reagents", Tetrahedron Letters 40 (1999) 2871-2874.
Liu et al., "Triethylaluminum- or Triethylborane-Induced Free Radical Reaction Alkyl Iodides and α,β-Unsaturated Compounds", J. Org. Chem. 2003, 68, 4030-4038.
Lutz et al., "Highly Enantioselective Addition of Mixed Diorganozincs to Aldehydes", J. Org. Chem. 1997, 62, 7895-7898.
Lutz et al., "Neopentyl and Neophyl Groups: New Nontransferable Groups for Organocopper and Organozinc Chemistry", Synthesis 1999, No. 2, 312-315 ISSN 0039-7881.
Mampreian et al., "Efficient Cu-Catalyzed Asymmetric Conjugate Additions of Alkylzinc Reagents to Aromatic and Aliphatic Acyclic Nitroalkenes", Organic Letters 2004, vol. 6, No. 16, 2829-2832.
Martin et al., "Highly Enantioselective Transfer hydrogenation of α,β-Unsaturated Ketones", J. Am. Chem. Soc. 2006, 128, 13368-13369.
Niwa et al., "Catalytic Asymmetric Synthesis of Optically Active Alkynyl Alcohols by enantioselective Alkynylation of Aldehydes and by Enantioselective Alkylation of Alkynyl Aldehydes", J. Chem. Soc. Perkin Trans 1, 1990 pp. 937-943.
Nugent, "MIB: an advantageous alternative to DAIB for the addition of organozinc reagents to aldehydes", Chem. Commun., 1999, 1369-1370.
Ohta et al., "Asymmetric Reduction of Nitro Olefins by Fermenting Bakers' Yeast", J. Org. Chem. 1989, 54, 1802-1804.
Oppolzer et al., "Catalytic Asymmetric Synthesis of Macrocyclic (E)-Allylic Alcohols from ω-Alkynals via Intramolecular 1-Alkenylzinc/Aldehyde Additions", J. Org. Chem. 2001, 66, 4766-4770.
Park et al., "Zinc-Catalyzed Enantioselective Hydrosilylation of Imines", Adv. Synth. Catal. 2006, 348, 1029-1032.
Alexakis et al., "Dramatic Improvement of the Enantiomeric Excess in the Asymmetric Conjugate Addition Reaction using New Experimental Conditions", J. Am. Chem. Soc. 2002, 124, 5262-5263.
Almansa et al., "Nickel-catalysed addition of dialkylzinc reagents to N-phosphinoyl- and N-sulfonylimines", Tetrahedron 63 (2007) 1167-1174.
Andersson et al., "Preparation and Use of Aziridino Alcohols as Promoters for the Enantioselective Addition of Dialkylzinc reagents to N-(Diphenylphosphinoyl) Imines", J. Org. Chem. 1997, 62, 7364-7375.
Bercot et al., "A Palladium-Catalyzed Enantioselective Alkylative Desymmetrization of meso-Succinic Anhydrides", J. Am. Chem. Soc. 2004, 126, 10248-10249.
Berger et al., "β-Snilyl Diorganozinc Compounds—A New Class of Useful Zinc Reagents", Angew. Chem. Int. Ed. Engl. 1997, 36, No. 13/14.

(Continued)

*Primary Examiner* — Porfirio Nazario Gonzalez

(57) ABSTRACT

There are provided methods for preparing diorganozinc compounds of formula $R_2Zn$. For example, such a method can method comprise reacting together a compound of formula $ZnX_2$ with at least one compound chosen from compounds of formulas $RM^1T$, $R_2M^1$, and $RM^2$. $R$, $X$, $M^1$, $M^2$, and $T$ can be various different chemical entities. Compounds of formula $R^2ZnR^3$, in which $R^2$ and $R^3$ are the same or different, can also prepared in a similar manner.

75 Claims, 1 Drawing Sheet

OTHER PUBLICATIONS

Berger et al., "R(Me3SiCH2)Zn—eine neue Klasse n}utzlicher Zinkverbindungen (R=Alkyl, Aryl)", Angew. Chem. 1997, 109, No. 13/14.

Bloch, "Additions of Organometallic Reagents to C=N Bonds: Reactivity and Selectivity", Chem. Rev. 1998, 98, 1407-1438.

Boezio et al., "Asymmetric, Catalytic Synthesis of α-Chiral Amines using a Novel Bis(phosphine) Monoxide Chiral Ligand", J. Am. Chem. Soc. 2003, 125, 14260-14261.

Bolm et al., "Asymmetric, Catalytic Phenyl Transfer to Aldehydes: Enantioselective Synthesis of Diarylmethanols", Angew. Chem. Int. Ed. 2000, 39, No. 19.

Bolm et al., "Asymmetric, Catalytic Phenyl Transfer to Aldehyde: Enantioselective Synthesis of Diarylmethanols", Angew. Chem. 2000, 112, No. 19.

Bolm et al., "Catalyzed Asymmetric Aryl Transfer Reactions to Aldehydes with Boronic Acids as Aryl Source", J. Am. Chem. Soc. 2002, 124, 14850-14851.

Buchowiecki et al., "1-Diphenylphosphinyl-2,2-Dimethylaziridine—A New Precursor of α,α-Dimethylarylalkylamines", Tetrahedron Letters, vol. 26, No. 9, pp. 1245-1248, 1985.

Carnes et al, "Synthesis, Isolation, and Chemical Reactivity Studies of Nanocrystalline Zinc Oxide", Langmuir 2000, 16, 3764-3772.

Charette et al., "Asymmetric catalytic addition of diorganozinc reagents to imines: Scope and application", Pure Appl. Chem., vol. 77, No. 7, pp. 1259-1267, 2005.

Choi et al., "Highly Enantioselective Copper-Catalyzed Conjugate Addition of Diethylzinc to Nitroalkenes", Organic Letter, 2004, vol. 6, No. 16, 2689-2691.

Coates et al., "Alkoxy-, Thio-, and Amino-derivatives of Methylzinc", Chemistry Department, University Science Laboratories, Durham, Received, Aug. 19, 1964, pp. 1870-1877.

Corey et al., "Enantioselective Conjugate Addition of Rationally Designed Chiral Cuprate Reagents to 2-Cycloalkenones", J. Am. Chem. Soc. 1986, 108, 7114-7116.

Côté et al., "Catalytic asymmetric addition of diorganozinc reagents to N-phosphinoylalkylimines", PNAS, Apr. 13, 2004, vol. 101, No. 15, 5405-5410.

Côté et al., "Application of the Chiral Bis(phosphine) Monoxide Ligand to Catalytic Enantioselective Addition of Dialkylzinc Reagents to β-Nitroalkenes", Organic Letters, 2007, vol. 9, No. 1, 85-87.

Côté et al., "General Method for the Expedient Synthesis of Salt-Fre Diorganozinc Reagents Using Methoxide", J. Am. Chem. Soc. 2008, 130, 2771-2773.

Dahmen et al., "[2,2]Paracyclophane-Based N,O-Ligands in Alkenylzinc Additions to Aldehydes", Organic Letter, 2001, vol. 3, No. 25, 4119-4122.

Degrado et al., "Modular Peptide-Based Phosphine Ligands in Asymmetric Catalysis: Efficient and Enantioselective Cu-Catalyzed Conjugate Additions to Five-, Six-, and Seven-Membered Cyclic Enones", J. Am. Chem. Soc. 2001, 123, 755-756.

Desrosiers et al., "Preparation of Enantiomerically Enriched (1S)-1-Phenylpropan-1-Amine Hydrochloride by a Catalytic Addition of Diorganozinc Reagents to Imines", Org. Synth. 2006, 83, 5-17.

Fabicon et al., "Formation of organozincate species from diorganozinc compounds and salts", J. Chem. Soc., Dalton Trans., 2001, 783-788.

Feringa et al., "Highly Enantioselective Catalytic Conjugate Addition and Tandem Conjugate Addition-Aldol Reactions of Organozinc Reagents", Angew. Chem. Int. Ed. Engl. 1997, 36, No. 23.

Feringa et al., "Hochenantioselektive Katalytische 1,4-Addition and Kombinierte 1,4-Addition/Aldolreaktion von Organo", Angew. Chem. 1997, 109, No. 23.

Gilman et al., "Cyclohexyl Carbinol", Organic Syntheses, Coll. vol. 1, p. 188 (1941); vol. 6, p. 22 (1926).

Gilman et al., "A Qualitative Color Test for the Grignard Reagent", Contribution from the Chemical Laboratory of Iowa State College, published on Jul. 3, 1925.

Graves et al., "Enantioselective MSPV Reduction of Ketimines Using 2-Propanol and (BINOL)Al III", Organic Letters, 2006, vol. 8, No. 6, 1229-1232.

Guijarro et al., "Enantioselective Addition of Dialkylzinc Reagents to N-(Diphenylphosphinoyl) Imines Promoted by 2-Azanorbornylmethanols", J. Org. Chem. 1998, 63, 2530-2535.

Guijarro, "Dynamic behavior or organozinc compounds", Book—The Chemistry of Organozinc Compounds, 2006, pp. 193-236.

Jeon et al., "Catalytic Asymmetric Synthesis of Hydroxy enol Ethers: Approach to a Two-Carbon Homologation of Aldehydes", Organic Letter, 2005, vol. 7, No. 9, 1729-1732.

Jeon et al., "Catalytic Asymmetric Addition of Alkylzinc and Functionalized Alkylzinc Reagents to Ketones", J. Org. Chem. 2005, 70, 448-455.

Jimeno et al., "The Dual-Catalyzed (Amino Alcohol/Lewis Acid) Enantioselective Addition of Diethylzinc to N-Diphenylphosphinoyl Imines", Tetrahedron Letters 40 (1999) 777-780.

Jones et al. "Conjugate Michael-additions with mixed diorganozincs", J. Chem. Soc. Perkin Trans. 1, 1997, 3117-3118.

Jones et al., "Conjugate Michael Additions with Mixed Diorganozincs", Tetrahedron 54 (1998) 1471-1490.

Kanai et al., "Catalytic Enantioselective Conjugate Addition of Grignard Reagents to Cyclic α, β-Unsaturated Carbonyl Compounds", Tetrahedron 55 (1999) 3843-3854.

Kitamura et al., "1,4-Addition of Diorganozincs to α, β-Unsaturated Ketones Catalyzed by a Copper(I)-Sulfonamide Combined System", Bull. Chem. Soc. Jpn., 73, 999-1014 (2000(.

Pinho et al., "Asymmetric addition of diethylzinc to N-(diphenylphosphinoyl) imines", Tetrahedron 57 (2001) 1615-1618.

Powell et al., "Anti-1,3-diols by Addition of Dialkylzinc Reagents to 4-Acetoxy-1,3-dioxanes", J. Org. Chem. 1999, 64, 2026-2037.

Pu et al., "Catalytic Asymmetric Organozinc Additions to Carbonyl Compounds", Chem. Rev. 2001, 101, 757-824.

Rieke et al., "Direct Formation and Reaction of Thienyl-Based Organocopper Reagents", J. Org. Chem. 1993, 58, 2492-2500.

Rimkus et al., "Conjugate Addition of Mixed Diorganozinc Compounds and Functionalized Organozinc Cuprates to Nitroolefins", Organic Letters 2002, vol. 4, No. 19, 3289-3291.

Rudolph et al., "Phenyl versus Ethyl Transfer in the Addition of Organozinc Reagents to aldehydes: A Theoretical Study", Angew. Chem. 2003, 115, 3110-3113.

Rudolph et al., "A High-Throughput Screening Approach for the Determination of Additive Effects in Organozinc Addition Reactions to Aldehydes", Adv. Synth. Catal. 2005, 347, 1361-1368.

Rudolph et al., "Phenyl versus Ethyl Transfer in the Addition of Organozinc Reagents to Aldehydes: A Theoretical Study", Angew. Chem. Int. Ed. 2003, 42, 3002-3005.

Sato et al., "Asymmetric synthesis of N-diphenylphosphinoylamines by solvent free enantioselective addition of dialkylzincs to N-diphenylphosphnoylimines", J. Chem. Soc., Perkin Trans. 1, 2001, 2912-2914.

Schmidt et al., "Catalytic asymmetric approaches towards enantiomerically enriched diarylmethanols and diarylmethylamines", Chem. Soc. Rev., 2006, 35, 454-470.

Soai et al., "Highly Enantioselective Alkylation of Carbon-Nitrogen Double Bonds, catalytic and Stoichiometric Asymmetric Synthesis of Optically Active amines by the Enantioselective Addition of Dialkylzinc Reagents to N-Diphenylphosphinoylimines", J. Chem. Soc., Chem. Commun., 1992, pp. 1097-1098.

Soai et al., "Enantioselective Addition of Organozinc Reagents to Aldehydes", Chem. Rev. 1992, 92. 833-856.

Soai et al., "Remarkable Effect of Alkylbenzenes as Solvents in Enantioselective Alkylation of N-Diphenylphosphinoylimines with Diethylzinc using Polystyrene Supported Ephedrine", J. Chem. Soc., Chem. Commun., 1994, pp. 317-318.

Soai et al., "Enantioselective addition of organozinc compounds", Book—The Chemistry of Organozinc Compounds, 2006, pp. 555-593.

Stangeland et al., "New Chiral Ligands for the Asymmetric Copper Catalyzed Conjugate Addition of Grignard Reagents to Enones", Tetrahedron, vol. 53, No. 48, pp. 16503-16510, 1997.

Suzuki et al., "Enantioselective addition of dialkylzinc to N-diphenylphosphinyl-imines using polymer-supported N, N-dialkylnorephedrines dialkylnorephedrines as chiral ligands", J. Chem. Soc., Perkin Trans. 1, 1997, pp. 2757-2760.

Suzuki et al., "Chiral amino alcohols bound to diimines, diamines and dendrimers as chiral ligands for the enantioslective ethylation of N-diphenylphosphinylimines", Tetrahedron: Asymmetry, vol. 8, No. 24, pp. 4033-4040, 1997.

Suzuki et al., "Enantioselective addition of dialkylzincs to N-diphenylphosphinyl-imines using polymer-supported N, N-dialkylnorephedrines as chiral ligands", J. Chem. Soc., Perkin Trans. 1, 1997, pp. 2757-2760.

Totleben et al., "Conjugate Addition Reactions of Organosamarium Species via in Situ Transmetalation to Cu(I) Salts", J. Org. Chem. 1992, 57, 1740-1744.

Tuttle et al., "Organocatalytic Transfer Hydrogenation of Cyclic Enones", J. Am. Chem. Soc. (2006), 128, 12662-12663.

Wang et al., "Chiral ferrocenyl amidophosphine ligand for highly enantioselelctive addition of diethylzinc to N-diphenylphosphinoylimines", Tetrahedron 62 (2006) 12220-12226.

Wipf et al., "Copper-Catalyzed Conjugate Additions of Organozirconocenes. Synthetic and Mechanistic Studies", Tetrahedron vol. 50, No. 7, pp. 1935-1954, 1994.

Wipf et al., "Preparation of Allylic Alcohols by Alkene Transfer from Zirconium to Zinc", Tetrahedron Letters, vol. 35, No. 29, pp. 5197-5200, 1994.

Zhang et al., "Enantioselective addition of diethylzinc to N-diphenylphosphinoylimines employing N,N-dialkyl-1,2-diphenyl-2-aminoethanols as chiral ligands", Tetrahedron Letters 42 (2001) 6369-6372.

Zhang et al., "Highly Enantioselective Diethylzinc Addition to Imines Employing Readily Available N-Monosubstituted Amino Alcohols", Organic Letters 2002, vol. 4, No. 8, 1399-1402.

Zhang et al., "Evaluation of Chiral Oxazolines for the Highly Enantioselective Diethylzinc Addition to N(Diphenylphosphinoyl) Imines", J. Org. Chem. 2003, 68, 4322-4329.

Zhou et al., Chiral Mercaptoaryl-oxazolines as ligands in Enantioselective Copper-Catalyzed 1,4-Additions of Grignard Reagents to Enones, Tetrahedron, vol. 50, No. 15, pp. 4467-4478 (1994).

Charette et al., "General Method of the Expedient Synthesis of Salt-Free Diorganozinc Reagents using Zinc Methoxide", J. Am. Chem. Soc. (2008), vol. 130, pp. 2771-2773.

English abstract of JP 02-129135 published on May 17, 1990.

English abstract of JP 4 221389 published on Aug. 11, 1992.

Bussche-Hunnefeld et al. "Enantioselective Preparation of sec. Alcohols from Aldehydes and Dialkyl Zinc Compounds, Generated in situ from Grignard Reagents, Uisng Substoichiometric Amounts of TADDOL-Titanates", Tetrahedron, vol. 48, No. 27, pp. 5719-5730, 1992.

* cited by examiner

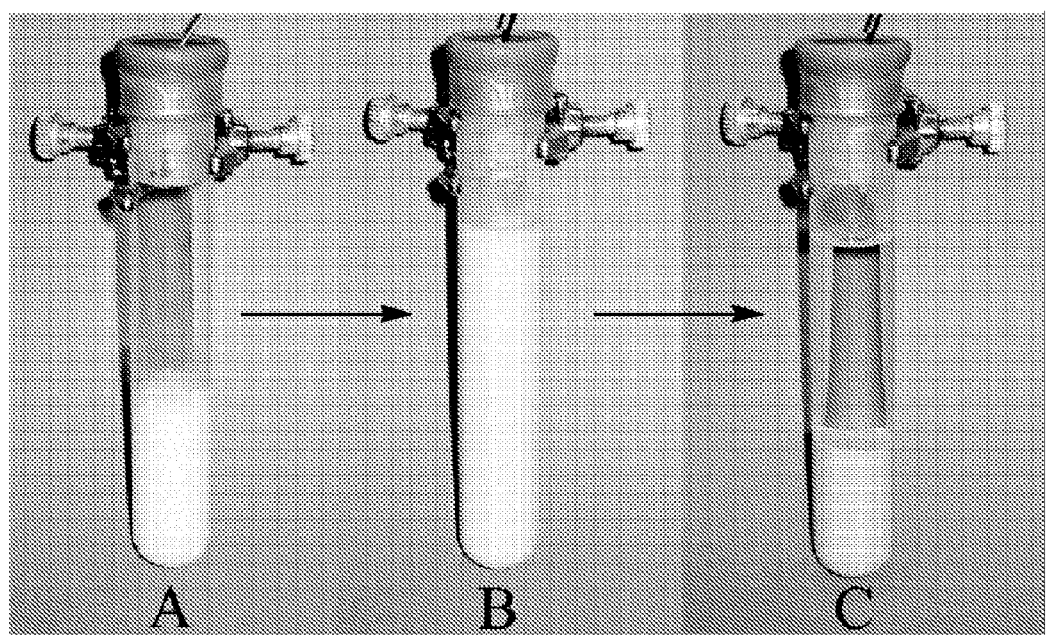
(A) Zn(OMe)$_2$ in Et$_2$O. (B) After addition in EtMgCl in Et$_2$O.
(C) After centrifugation.

METHODS FOR PREPARING DIORANOZINC COMPOUNDS

CROSS-REFERENCE TO RELATED APPLICATIONS

The present application is a continuation-in-part of International Patent Application no. PCT/CA2008/000864 filed on May 6, 2008, which claims priority to U.S. Provisional Application No. 60/916,419 filed on May 7, 2007. The above-mentioned applications are incorporated herein by reference in their entirety.

TECHNICAL FIELD

The present document relates to improvements in the field chemistry. In particular, it relates to a method for preparing diorganozinc compounds.

BACKGROUND OF THE DISCLOSURE

Finding the right balance between reactivity and selectivity is one of the greatest scientific challenges in modern chemistry. In this context, diorganozinc reagents have proven effective in asymmetric catalysis.[i] Although, this family of organometallic reagents has been known for years, the synthesis of functionalized diorganozinc compounds has, only recently, made some significant progress, beginning with the seminal work of Knochel and co-workers.[ii] However, these functionalized diorganozinc reagents are widely underused in asymmetric catalysis, especially in non-academic laboratories. One explanation for this observation is mainly that current methods for preparing them (Equations 1 to 3) are somewhat troublesome. One must deal with (1) the potential hazards caused by the handling and distillation of highly pyrophoric chemicals and/or with (2) the presence of by-products, which are sometimes in stoichiometric amount and incompatible with catalytic reactions.[iii] Depending on the synthetic method used, the main by-products are either salts,[iv] residual organometallic species such as boranes,[v] or simply an excess of reagent.[vi] Even if some diorganozinc compounds can be purified through simple distillation or sublimation, the approach remains tedious and limited to volatile and low functionalized compounds.

$$R\text{-Metal} + ZnX_2 \rightarrow R_2Zn + \text{Metal-X} \qquad (1)$$

$$R^1\text{-Metal} + ZnR^2{}_2 \rightarrow R^1{}_2Zn + \text{Metal-}R^2 \qquad (2)$$

$$R^1\text{—X} + R^2{}_2Zn \rightarrow R^1{}_2Zn + R^2\text{—X} \qquad (3)$$

SUMMARY OF THE DISCLOSURE

According to one aspect, there is provided a method for preparing a compound of formula (I):

$$R_2Zn \qquad (I)$$

wherein
R is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_3$-$C_{20}$ carboxylic acid amide, $C_3$-$C_{12}$ cycloalkyl, $C_1$-$C_{12}$ heteroaryl, or a $C_1$-$C_{12}$ heterocyclyl, the method comprising reacting a compound of formula (II) with at least one compound chosen from compounds of formulas (IIIa), (IIIb), and (IIIc):

$$ZnX_2 \qquad (II)$$

$$RM^1T \qquad (IIIa)$$

$$R_2M^1 \qquad (IIIb)$$

$$RM^2 \qquad (IIIc)$$

$$MOR^6 \qquad (VI)$$

wherein
X is chosen from —$OR^1$, —$SR^1$, Cl, Br, I, $C_2$-$C_{20}$ alkylcarboxylate, $C_2$-$C_{12}$ heteroarylcarboxylate, and $C_6$-$C_{20}$ arylcarboxylate, and when X is Cl or Br, a compound of formula (VI) is further added;
R is as previously defined;
M is Na or K;
$M^1$ is Mg, Mn, Zr, Ti, or Ni;
$M^2$ is Li, or Na;
T is F, Cl, Br, I, $OSO_2R$, OR, CN, or OC(O)R;
$R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or
the two $R^1$ groups are linked together so as to form a 5 to 8 membered ring; and
$R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent which is compatible with a diorganozinc compound. Such a substituent can be chosen from a halogen (for example F, Cl, Br, or I) atom, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group.

According to another aspect, there is provided a method for preparing a compound of formula (Ia):

$$R^2ZnR^3 \qquad (Ia)$$

wherein
$R^2$ and $R^3$ are the same or different and they represent $C_1$-$C_{20}$ alkyl, $C_1$-$C_{20}$ haloalkyl $C_2$-$C_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_4$-C$_{30}$ alkylsilylalkyl, C$_9$-C$_{30}$ (alkyl)(aryl)silylalkyl, C$_{19}$-C$_{30}$ arylsilylalkyl, C$_4$-C$_{30}$ (alkyl)(heteroaryl)silylalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or C$_1$-C$_{12}$ heterocyclyl, the method comprising reacting a compound of formula (II) with at least one compound chosen from compounds of formulas (IIId), (IIIe), and (IIIf), and a least compound chosen from compounds of formulas (IIIg), (IIIh), and (IIIi), or with a compound of formula (IIIj):

$$ZnX_2 \quad (II)$$

$$R^2M^1T \quad (IIId)$$

$$(R^2)_sM^1 \quad (IIIe)$$

$$R^2M^2 \quad (IIIf)$$

$$R^3M^1T \quad (IIIg)$$

$$(R^3)_2M^1 \quad (IIIh)$$

$$R^3M^2 \quad (IIIi)$$

$$R^2M^1R^3 \quad (IIIj)$$

$$MOR^6 \quad (VI)$$

wherein

X is chosen from —OR$^1$, —SR$^1$, Cl, Br, I, C$_2$-C$_{20}$ alkylcarboxylate, C$_2$-C$_{12}$ heteroarylcarboxylate, and C$_6$-C$_{20}$ arylcarboxylate and when X is Cl or Br, a compound of formula (VI) is further added;

R$^2$ and R$^3$ are as previously defined;

M is Na or K;

M$^1$ is Mg, Mn, Zr, Ti, or Ni;

M$^2$ is Li, or Na;

T is F, Cl, Br, I, OSO$_2$R$^2$, OR$^2$CN, or OC(O)R$^2$;

R$^1$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, or the two R$^1$ groups are linked together so as to form a 5 to 8 membered ring; and R$^6$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent which is compatible with a diorganozinc compound. Such a substituent can be chosen from a halogen (for example F, Cl, Br, or I) atom, a deuterium atom, a tritium atom, —OH, —CN, —NO$_2$, —SH, —OR, —SR, C$_1$-C$_6$ alkoxy, C$_1$-C$_3$ alkyl, C$_2$-C$_8$ alkenyl, C$_2$-C$_3$ alkynyl, C$_1$-C$_6$ aminoalkyl, C$_6$-C$_{20}$ aralkyl, C$_6$-C$_{12}$ aryl, C$_3$-C$_8$ cycloalkyl, C$_1$-C$_{12}$ heteroaryl, C$_1$-C$_{12}$ heterocyclyl, C$_2$-C$_{20}$ carboxylic acid ester, C$_3$-C$_{20}$ carboxylic acid amide, C$_1$-C$_6$ hydroxyalkyl, C$_2$-C$_3$ cyclic acetal, C$_1$-C$_{12}$ acetal, C$_1$-C$_{12}$ acyclic orthoester, C$_4$-C$_6$ cyclic orthoester, C$_1$-C$_{12}$ sulfone, C$_1$-C$_{12}$ sulfoxide, C$_2$-C$_{12}$ carbamate, C$_2$-C$_{12}$ urea, C$_2$-C$_{12}$ sulfonamide, C$_2$-C$_{12}$ sulfoxamide, C$_2$-C$_{12}$ phosphonate, C$_2$-C$_{12}$ phosphinoyl, C$_2$-C$_{12}$ hydroxamic acid ester, and a suitable protecting group.

According to another aspect, there is provided a method for preparing a compound of formula (Ia):

$$R^2ZnR^3 \quad (Ia)$$

wherein

R$^2$ and R$^3$ are the same or different and they represent a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_4$-C$_{30}$ alkylsilylalkyl, C$_9$-C$_{30}$ (alkyl)(aryl)silylalkyl, C$_{19}$-C$_{30}$ arylsilylalkyl, C$_4$-C$_{30}$ (alkyl)(heteroaryl)silylalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, the method comprising reacting a compound of formula (IIa) with a compound of formula (IIIg), and a compound of formula (VI):

$$R^2ZnX \quad (IIa)$$

$$R^3M^1T \quad (IIIg)$$

$$MOR^6 \quad (VI)$$

wherein

X is chosen from —OR$^1$, —SR$^1$, Cl, Br, I, C$_2$-C$_{20}$ alkylcarboxylate, C$_2$-C$_{12}$ heteroarylcarboxylate, and C$_6$-C$_{20}$ arylcarboxylate;

R$^2$ and R$^3$ are as previously defined;

M$^1$ is Mg, Mn, Zr, Ti, or Ni;

M is Na or K;

T is F, Cl, Br, I, OSO$_2$R$^2$, OR, CN, or OC(O)R$^2$;

R$^1$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl; and R$^6$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent which is compatible with a diorganozinc compound. Such a substituent can be chosen from a halogen (for example F, Cl, Br, or I) atom, a deuterium atom, a tritium atom, —OH, —CN, —NO$_2$, —SH, —OR, —SR, C$_1$-C$_6$ alkoxy, C$_1$-C$_8$ alkyl, C$_2$-C$_8$ alkenyl, C$_2$-C$_8$ alkynyl, C$_1$-C$_6$ aminoalkyl, C$_6$-C$_{20}$ aralkyl, C$_6$-C$_{12}$ aryl, C$_3$-C$_8$ cycloalkyl, C$_1$-C$_{12}$ heteroaryl, C$_1$-C$_{12}$ heterocyclyl, C$_2$-C$_{20}$ carboxylic acid ester, C$_3$-C$_{20}$ carboxylic acid amide, C$_1$-C$_6$ hydroxyalkyl, C$_2$-C$_3$ cyclic acetal, C$_1$-C$_{12}$ acetal, C$_1$-C$_{12}$ acyclic orthoester, C$_4$-C$_6$ cyclic orthoester, C$_1$-C$_{12}$ sulfone, C$_1$-C$_{12}$ sulfoxide, C$_2$-C$_{12}$ carbamate, C$_2$-C$_{12}$ urea, C$_2$-C$_{12}$ sulfonamide, C$_2$-C$_{12}$ sulfoxamide, C$_2$-C$_{12}$ phosphonate, C$_2$-C$_{12}$ phosphinoyl, C$_2$-C$_{12}$ hydroxamic acid ester, and a suitable protecting group.

According to another aspect, there is provided a method for preparing a substantially salt-free diorganozinc compound of formula (I) or a substantially salt-free composition comprising a diorganozinc compound of formula (I) and at least one solvent:

R$_2$Zn  (I)

wherein

R is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_r$-C$_{20}$ alkylaminoalkyl, C$_4$-C$_{30}$ alkylsilylalkyl, C$_9$-C$_{30}$ (alkyl)(aryl)silylalkyl, C$_{19}$-C$_{30}$ arylsilylalkyl, C$_4$-C$_{30}$ (alkyl)(heteroaryl)silylalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, the method comprising:

reacting a compound of formula (II) with at least one compound chosen from compounds of formulas (IIIa), (IIIb), and (IIIc) optionally in the presence of at least one solvent so as to obtain an intermediate composition and then, reacting a compound of formula (VI) with the intermediate composition so as to obtain a mixture comprising a solid phase and a liquid phase or at least two solids;

ZnX$_2$  (II)

RM$^1$T  (IIIa)

R$_2$M$^1$  (IIIb)

RM$^2$  (IIIc)

MOR$^6$  (VI)

wherein

X is chosen from —OR$^1$, —SR$^1$, Cl, Br, I, C$_2$-C$_{20}$ alkylcarboxylate, C$_2$-C$_{12}$ heteroarylcarboxylate, and C$_6$-C$_{20}$ arylcarboxylate;

R is as previously defined;

M is Na or K;

M$^1$ is Mg, Mn, Zr, Ti, or Ni;

M$^2$ is Li, or Na;

T is F, Cl, Br, I, OSO$_2$R, CN, OR or OC(O)R;

R$^1$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, or the R$^1$ are linked together so as to form a 5 to 8 membered ring; and R$^6$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_r$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, —OH, —CN, —NO$_2$, —SH, —OR, —SR, C$_1$-C$_6$ alkoxy, C$_1$-C$_8$ alkyl, C$_2$-C$_8$ alkenyl, C$_2$-C$_8$ alkynyl, C$_1$-C$_6$ aminoalkyl, C$_6$-C$_{20}$ aralkyl, C$_6$-C$_{12}$ aryl, C$_3$-C$_8$ cycloalkyl, C$_1$-C$_{12}$ heteroaryl, C$_1$-C$_{12}$ heterocyclyl, C$_2$-C$_{20}$ carboxylic acid ester, C$_3$-C$_{20}$ carboxylic acid amide, C$_1$-C$_6$ hydroxyalkyl, C$_2$-C$_3$ cyclic acetal, C$_1$-C$_{12}$ acetal, C$_1$-C$_{12}$ acyclic orthoester, C$_4$-C$_6$ cyclic orthoester, C$_1$-C$_{12}$ sulfone, C$_1$-C$_{12}$ sulfoxide, C$_2$-C$_{12}$ carbamate, C$_2$-C$_{12}$ urea, C$_2$-C$_{12}$ sulfonamide, C$_2$-C$_{12}$ sulfoxamide, C$_2$-C$_{12}$ phosphonate, C$_2$-C$_{12}$ phosphinoyl, C$_2$-C$_{12}$ hydroxamic acid ester, and a suitable protecting group;

separating the solid phase and the liquid phase from one another or separating the at least two solids from one another; and optionally substantially removing at least a portion of the solvent from the liquid phase.

According to another aspect, there is provided a method for preparing a substantially salt-free diorganozinc compound of formula (Ia) or a substantially salt-free composition comprising a diorganozinc compound of formula (Ia) and at least one solvent:

R$^2$ZnR$^3$  (Ia)

wherein

R$^2$ and R$^3$ are the same or different and they represent C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_4$-C$_{30}$ alkylsilylalkyl, C$_9$-C$_{30}$ (alkyl)(aryl)silylalkyl, C$_{19}$-C$_{30}$ arylsilylalkyl, C$_4$-C$_{30}$ (alkyl)(heteroaryl)silylalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or C$_1$-C$_{12}$ heterocyclyl, the method comprising:

reacting a compound of formula (II) with at least one compound chosen from compounds of formulas (IIId), (IIIe), and (IIIf), and a least compound chosen from compounds of formulas (IIIg), (IIIh), and (IIIi), or with a compound of formula (IIIj), optionally in the presence of at least one solvent so as to obtain an intermediate composition and then, reacting a compound of formula (VI) with the intermediate composition so as to obtain a mixture comprising a solid phase and a liquid phase or at least two solids;

ZnX$_2$  (II)

R$^2$M$^1$T  (IIId)

$(R^2)_2M^1$ (IIIe)

$R^2M^2$ (IIIf)

$R^3M^1T$ (IIIg)

$(R^3)_2M^1$ (IIIh)

$R^3M^2$ (IIIi)

$R^2M^1R^3$ (IIIj)

$MOR^6$ (VI)

wherein
X is chosen from $-OR^1$, $-SR^1$, Cl, Br, I, $C_2$-$C_{20}$ alkylcarboxylate, $C_2$-$C_{12}$ heteroarylcarboxylate, and $C_6$-$C_{20}$ arylcarboxylate;
$R^2$ and $R^3$ are as previously defined;
M is Na or K;
$M^1$ is Mg, Mn, Zr, Ti, or Ni;
$M^2$ is Li, or Na;
T is F, Cl, Br, I, $OSO_2R^2$, $OR^2CN$, or $OC(O)R^2$;
$R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or
the two $R^1$ groups are linked together so as to form a 5 to 8 membered ring; and
$R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl,
the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent which is compatible with a diorganozinc compound. Such a substituent can be chosen from a halogen (for example F, Cl, Br, or I) atom, a deuterium atom, a tritium atom, $-OH$, $-CN$, $-NO^2$, $-SH$, $-OR$, $-SR$, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_3$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group,
separating the solid phase and the liquid phase from one another or separating the at least two solids from one another; and
optionally substantially removing at least a portion of the solvent from the liquid phase.

According to another aspect, there is provided a method for preparing a substantially salt-free diorganozinc compound of formula (I) or a substantially salt-free composition comprising a diorganozinc compound of formula (I) and at least one solvent:

$R_2Zn$ (I)

wherein
R is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl,
the method comprising:
reacting a composition comprising compound of formula (I) and a compound of formula (VII) with a compound of formula (VI) optionally in the presence of a solvent so as to obtain a mixture comprising a solid phase and a liquid phase or at least two solids;

$MOR^6$ (VI)

$M^1X_2$ (VII)

wherein
X is chosen from $-OR^1$, $-SR^1$, Cl, Br, I, $C_2$-$C_{20}$ alkylcarboxylate, $C_2$-$C_{12}$ heteroarylcarboxylate, and $C_6$-$C_{20}$ arylcarboxylate;
M is Na or K;
$M^1$ is Mg, Mn, Zr, Ti, or Ni;
$R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or
the $R^1$ are linked together so as to form a 5 to 8 membered ring; and
$R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_r$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl,
the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, $-OH$, $-CN$, $-NO_2$, $-SH$, $-OR$, $-SR$, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group;

separating the solid phase and the liquid phase from one another or separating the at least two solids from one another; and optionally substantially removing at least a portion of the solvent from the liquid phase.

According to another aspect, there is provided a method for preparing a substantially salt-free diorganozinc compound of formula (Ia) or a substantially salt-free composition comprising a diorganozinc compound of formula (Ia) and at least one solvent:

$$R^2ZnR^3 \quad (Ia)$$

wherein $R^2$ and $R^3$ are the same or different and they represent $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or $C_1$-$C_{12}$ heterocyclyl, the method comprising:

reacting a composition comprising at least one compound of formula (Ia) and at least one compound of formula (VII) with a compound of formula (VI) optionally in the presence of a solvent so as to obtain a mixture comprising a solid phase and a liquid phase or at least two solids;

$$MOR^6 \quad (VI)$$

$$M^1X_2 \quad (VII)$$

wherein

X is chosen from —$OR^1$, —$SR^1$, Cl, Br, I, $C_2$-$C_{20}$ alkylcarboxylate, $C_2$-$C_{12}$ heteroarylcarboxylate, and $C_6$-$C_{20}$ arylcarboxylate;

M is Na or K;

$M^1$ is Mg, Mn, Zr, Ti, or Ni;

$R^1$ is a $C_1$-$C_{20}$, alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or the $R^1$ are linked together so as to form a 5 to 8 membered ring; and $R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group;

separating the solid phase and the liquid phase from one another or separating the at least two solids from one another; and optionally substantially removing at least a portion of the solvent from the liquid phase.

It was found that such methods can be applied to a wide scope of reactions. It was also found that such a method is an efficient, safe and general method for preparing diorganozinc reagents while eliminating substantially all by-products. Advantages such as the high reactivity of certain intermediates, for example organomagnesium reagents, their readily commercial availability and their ease of preparation and handling, permits to easily employ them as main precursors for diorganozinc reagents synthesis. These two methods can be used under the same reaction conditions.

According to another aspect, there is provided a method for preparing a compound of formula (IV):

$$Zn(OR^1)_2 \quad (IV)$$

wherein $R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or the two $R^1$ groups are linked together so as to form a 5 to 8 membered ring;

the alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from a halogen (for example F, Cl, Br, or I) atom, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group, the method comprising reacting a compound of formula (II) with a compound of formula (V):

$$ZnX_2 \quad (II)$$

$$MOR^1 \quad (V)$$

wherein

X is Cl, Br or I;

M is Na or K; and $R^1$ is as previously defined.

BRIEF DESCRIPTION OF THE DRAWINGS

Further features and advantages will become more readily apparent from the following description of various embodiments as illustrated by way of examples in the appended drawings wherein:

FIG. 1 is a picture taken during the preparation of $Et_2Zn$, wherein (A) represents $Zn(OMe)_2$ in diethylether, (B) represents a mixture of $Zn(OMe)_2$ in diethylether into which EtMgCl in diethylether has been added, and (C) represents the mixture shown in (B) after centrifugation, the liquid phase comprising $Et_2Zn$ and diethylether and the solid phase or precipitate comprising at least one magnesium salt chosen from $Mg(OMe)_2$, MgCl(OMe), $MgCl_2$, and mixtures thereof.

DETAILED DESCRIPTION OF VARIOUS EMBODIMENTS

The expression "glyme-type solvent" as used herein can refer to various solvents. For example, a glyme-type solvent can be one of formula $R^4O(CH_2CH_2O)_nR^5$ in which n is 1, 2, or 3, $R^4$ and $R^5$ are the same or different and they represent a $C_1$-$C_4$ alkyl.

The term "alkyl" as used herein refers to a straight or branched alkyl.

The term "aryl" as used herein refers to a cyclic or polycyclic aromatic ring.

The term "heteroaryl" as used herein refers to an aromatic cyclic or fused polycyclic ring system having at least one heteroatom selected from the group consisting of N, O, and S. For example, the heteroaryl group can be furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The term "heterocyclyl" includes non-aromatic rings or ring systems that contain at least one ring having an at least one hetero atom (such as nitrogen, oxygen or sulfur). For example, this term can include all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The term "cycloalkyl" as used herein refers to a hydrocarbon ring which may contain or not double bonds.

The expression "suitable protecting group" refers to any suitable protecting group for a given group and described by Wuts, Peter G. M., Greene Theodora W. in *Greene's Protective Groups in Organic Synthesis*, John Wiley & Sons, $4^{th}$ edition, December 2006, which is hereby incorporated by reference in its entirety. For example, the given group can be the hydroxy group of an hydroxyalkyl, the thiol group of a thioalkyl, the amino group of an aminoalkyl, the alkyne group of an alkynyl etc. Suitable protecting groups for an hydroxy group can be, for example, silyls (such as trimethylsilyl (TMS), triethylsilyl (TES), t-butyldimethylsilyl (TBDMS), t-butyldiphenylsilyl (TBDPS)).

The expression "substantially salt-free" when related to a diorganozinc compound or to a composition comprising a diorganozinc compound refers, for example, to a compound or a composition in which there is less than about 0.15 equivalent of salt per equivalent of diorganozinc. For example, such a compound or composition can comprise less than about 0.1, 0.05, or 0.01 equivalent of salt per equivalent of diorganozinc.

When preparing a compound of formula (I) or (Ia) the reaction can be carried out in an organic solvent chosen from diethylether, t-butylmethylether, dibutylether, diphenylether, diisopropylether, dipropylether, dipentylether, dimethoxymethane, cyclopentylmethylether, diethoxymethane, derivatives thereof analogues thereof, and mixtures thereof. Alternatively, the organic solvent can be chosen from glyme-type solvents. Another organic solvent can be further added to the organic solvent. The other organic solvent being chosen from $C_1$-$C_{10}$ hydrocarbons for example toluene, benzene, hexanes, pentane, and heptane.

The compound of formula (II) and the compound(s) of formula (s) (IIIa)-(IIIi) can be reacted together in the organic solvent and agitated. The same can also be applied to compounds of formulas (IIa), (IIIg) and (VI).

The compound of formula (II) can be reacted with the compounds of formulas (IIIa) (IIIb), (IIIc), (IIId), (IIIe), (IIIf), (IIIg), (IIIh), (IIIi), (IIIj) by preparing a composition comprising the compound of formula (II) and the organic solvent, by adding the at least one compound chosen from compounds of formulas (IIIa) (IIIb), (IIIc), (IIId), (IIIe), (IIIf), (IIIg), (IIIh), (IIIi) and (IIIj) to the composition so as to obtain a mixture, and by agitating the mixture. The same can also be applied to compounds of formulas (IIa), (IIIg) and (VI).

The compound of formula (II) can also be reacted with at least one compound chosen from compounds of formulas (IIIa) (IIIb), (IIIc), (IIId), (IIIe), (IIIf), (IIIg), (IIIh), (IIIi), and (IIIj) by preparing a composition comprising the compound of formula (II) and the organic solvent, and by adding the at least one compound chosen from compounds of formulas (IIIa) (IIIb), (IIIc), (IIId), (IIIe), (IIIf), (IIIg), (IIIh), (IIIi), and (IIIj) dissolved in the organic solvent to the composition so as to obtain a mixture, and by agitating the mixture. The same can also be applied to compounds of formulas (IIa), (IIIg) and (VI).

When preparing a compound of formula (I) or (Ia), a precipitate comprising at least one compound chosen from $M^1X_2$, $M^1XT$, $M^2X_2$, and $M^2XT$ can be formed. A liquid phase comprising the compound of formula (I) can be at least partially separated from the precipitate. The mixture so-obtained can be centrifuged or filtered so as to separate the precipitate from the liquid phase comprising the compound of formula (I) or (Ia).

When preparing a compound of formula (Ia), a precipitate comprising a compound of formula $TM^1OR^1$ can be formed. The mixture so-obtained can be centrifuged or filtered so as to separate the precipitate from a liquid phase comprising the compound of formula (Ia).

The compound of formula (II) can be reacted with at least one compound chosen from compounds of formulas (IIIa) (IIIb), (IIIc), (IIId), (IIIe), (IIIf), (IIIg), (IIIh), (IIIi), and (IIIj) at a temperature of about −20° C. to about 35° C. or a temperature of about 0° C. The reaction can be carried out at a temperature of about 0° C. over a period of time of at least 5 minutes and then a heterogeneous solution so obtained can be allowed to stir at room temperature for a period of at least 5 minutes. The same can also be applied to compounds of formulas (IIa), (IIIg) and (VI).

For example, when preparing a compound of formula (I), the compound of formula (II) can be reacted with at least one compound chosen from compounds of formulas (IIIa), (IIIb), and (IIIc) so as to obtain an intermediate composition and then, the compound of formula (VI) can be reacted with the intermediate composition.

For example, when preparing a compound of formula (Ia), the compound of formula (II) can be reacted with at least one compound chosen from compounds of formulas (IIId), (IIIe), and (IIIf), and at least one compound chosen from compounds of formulas (IIIg), (IIIh), and (IIIi), or with a compound of formula (IIIj), so as to obtain an intermediate composition and then, the compound of formula (VI) can be reacted with the intermediate composition.

For example, when preparing a compound of formula (Ia), the compound of formula (IIa) can be reacted with a compound of formulas (IIIg) so as to obtain an intermediate composition and then, the compound of formula (VI) can be reacted with the intermediate composition.

For example, compound of formula (IIa) can be reacted with the compound of formula (IIIg) so as to obtain an intermediate composition and then, the compound of formula (VI) is reacted with the intermediate composition.

For example, compound of formula (IIa) can be reacted with the compound of formula (VI) so as to obtain an intermediate composition and then, the compound of formula (IIIg) is reacted with the intermediate composition.

For example, the methods of the present disclosure can be carried out in the presence or in the absence of a solvent. When carrying out a method in the absence of solvent, the obtained product is a neat product. When carrying out a method in the presence of at least one solvent, a composition comprising the desired compound and the at least one solvent is obtained. Such a composition can be concentrated by evaporation, distillation, filtration membrane etc. Moreover, the solvent can substantially be removed from the composition in order to obtain the final product in a neat form.

For example, when a mixture comprising at least two solids is obtained, it is possible to separate the at least two solids (such as a diorganozinc and at least one salt) from one another. In fact, it is possible, for example, to carry out a distillation or sublimation so as to selectively remove the diorganozinc compound from the rest of the mixture. For example, the obtained diorganozinc can have a melting point and/or a boiling point which is lower than the melting point and/or boiling point of the salts contained in the rest of the mixture.

For example, R, $R^2$ or $R^3$ can be chosen from a $C_1$-$C_{12}$ alkyl, $C_8$-$C_{12}$ arylalkyl, $C_6$-$C_{10}$ aryl, $C_4$-$C_{30}$ alkylsilylhydroxyalkyl and $C_3$-$C_6$ cycloalkyl. Alternatively, R, $R^2$ or $R^3$ is chosen from a $C_2$-$C_{10}$ alkyl, $C_8$-$C_{12}$ arylalkyl, benzyl, phenylethyl, phenyl, and $C_5$-$C_6$ cycloalkyl.

For example, X can be —$OR^1$ in which $R^1$ is a $C_1$-$C_{12}$ alkyl, $C_2$-$C_{12}$ haloalkyl, $C_3$-$C_{12}$ alkoxyalkyl, $C_1$-$C_{12}$ alkylaminoalkyl, or $C_2$-$C_{12}$ acyl. Alternatively, X can be —$OR^1$ in which $R^1$ is $RO(CH_2CH_2O)_nCH_2CH_2$— in which R is as previously defined and n is 1, 2 or 3.

For example, X can be —$OR^1$ in which $R^1$ is $CH_3$—, n-$C_5H_{11}$, $(CH_3)_2CH$—, $CH_3C(O)$—, PhC(O)—, $CF_3CH_2$—, $CH_3OCH_2CH_2$—, $CH_3OCH_2CH_2OCH_2CH_2$—, or $(CH_3)_2NCH_2CH_2$—. Alternatively, X can be —$OR^1$ in which $R^1$ is —$CH_3$, n-$C_5H_{11}$, $CH_3C(O)$—, PhC(O)—, $CF_3CH_2$—, $CH_3OCH_2CH_2$—, $CH_3OCH_2CH_2OCH_2CH_2$—, or $(CH_3)_2NCH_2CH_2$—. X can also be is acetylacetonate. The compound of formula (II) can also be $Zn(OCH_2CH_2O)$.

When preparing a compound of formula (I) R can be, for example, chosen from a $C_2$-$C_{20}$ alkenyl, $C_2$-$C_{20}$ alkynyl, $C_6$-$C_{20}$ alkylaryl, and $C_6$-$C_{12}$ aryl, X can be —OMe, and wherein the compound of formula (II) and at least one compound of formula (IIIa), (IIIb) or (IIIc) can be reacted together in the presence of NaOMe. Alternatively, R can be for example phenyl, X can be —OMe, and wherein the compound of formula (II) and the at least one compound of formula (IIIa), (IIIb) or (IIIc) can be reacted together in the presence of NaOMe.

For example, the compound of formula (II) can be reacted with a compound of formula (IIIa) in which T is Cl, Br or I.

The method for preparing a compound of formula (I) or (Ia) can further comprise carrying out a nucleophilic addition on an organic substrate by contacting the compound of formula (I) or (Ia) with the organic substrate in the presence or in the absence of a metal. The method can also further comprise carrying out a nucleophilic addition on an organic substrate by contacting the compound of formula (I) or (Ia) with the organic substrate in the presence of a metal and a ligand. For example, the metal can be Cu, Ti, Ni, or Zr. The nucleophilic addition can be a catalytic enantioselective addition. For example, the ligand can be a chiral ligand chosen from Me-DuPHOS(O), morpholino isoborneol (MIB), dimethylaminoisoborneol (DAIB), other amino alcohol based ligands, Josiphos, binap, bis(phosphine), taddol, bis(oxazoline), phosphoramidites, phosphites, diamines, PHOX, Binap(O), Binaphtol, and peptide based ligands. The nucleophilic addition can be carried out on an imine, an aldehyde, a ketone, or a β-nitroalkene of the organic substrate. The nucleophilic addition can also be a 1-4 addition carried out on an α,β-unsaturated aldehyde or an α,β-unsaturated ketone.

The method for preparing a compound of formula (I) or (Ia) can further comprise carrying out a chemical reaction chosen from an oxidation of a diorganozinc into an alcohol, nucleophilic allylic substitution ($S_N2'$), a transition metal catalyzed cross-coupling (for example nickel catalyzed cross-coupling or palladium catalyzed cross-coupling), a nucleophilic substitution (for example $S_N2$ on a ketal), an acylation, an anhydride opening, a carbozincation of an alkene or an alkyne, an allylzincation of alkenylmetal/metalla-aza-claisen, preparation of organozinc or organozinc halides, a cyclopropanation and an epoxidation, by using the compound of formula (I) or (Ia).

When preparing a compound of formula (IV), a compound of formula (II) can be reacted with a compound of formula (V) in the presence of an organic solvent chosen from diethylether, t-butylmethylether, dibutylether, diphenylether, diisopropylether, dipropylether, dipentylether, dimethoxymethane, cyclopentylmethylether, diethoxymethane, derivatives thereof, analogues thereof, and mixtures thereof. Alternatively, the organic solvent can be chosen from glyme-type solvents. Another organic solvent can further be added to the organic solvent. The other organic solvent can be chosen from $C_1$-$C_{10}$ hydrocarbons such as toluene, benzene, hexanes, pentane, and heptane. For example, M can be Na and X can be Cl.

The compounds of formulas (V) and (VI) can be the same. For example, both can represent NaOR or KOR in which R is a $C_1$-$C_{10}$ alkyl.

The person skilled in the art would clearly recognize that the processes for preparing compounds of formula (Ia) is similar to the process for preparing compounds of formula (I). In fact, the particular embodiments and examples previously mentioned concerning the process for preparing compounds of formula (I), when possible, can all be applied to the processes for preparing compounds of formula (Ia).

The following examples represent in a non-limitative manner, various embodiments.

Since the addition of a Grignard reagent on a zinc salt potentially generates several organic, organometallic and inorganic species, some of which are actually in equilibrium with each other[vii] and since it is difficult to accurately dose organometallic and inorganic impurities found in diorganozinc solutions, several tests have been carried out by using the prepared $R_2Zn$ solution in the catalytic enantioselective addition to imines.[viii] This reaction is known to be very sensitive to the presence of salts.

TABLE 1

Zinc Salts Screening

ZnX$_2$ + EtMgCl in Et$_2$O
(2 equiv)    (3.95 equiv)

↓ Et$_2$O

[Et$_2$Zn + Mg salt(s) ↓]

↓ Centrifugation or filtration

Et$_2$Zn in Et$_2$O
(R,R)-Me-BozPHOs™ (5 mol %)
Cu(OTf)$_2$ (10 mol %)
Toluene, 0° C., 16 h

| Entry | X | Yield [%][a] | ee [%][b] |
|---|---|---|---|
| 1 | none[c] | >95 | 0 |
| 2 | Cl | 51 | 27 |
| 3 | MeO | 95 | 97 |
| 4 | CF$_3$CH$_2$O | 46 | 10 |
| 5 | iPrO | 83 | 0 |
| 6 | CH$_3$OCH$_2$CH$_2$O | 88 | 97 |
| 7 | CH$_3$OCH$_2$CH$_2$OCH$_2$CH$_2$O | 65 | 88 |
| 8 | (CH$_3$)$_2$NCH$_2$CH$_2$O | 78 | 2 |
| 9 | Acac | 44 | 55 |
| 10 | nC$_5$H$_{11}$O | 45 | 41 |
| 11 | AcO | 94 | 97 |
| 12 | BzO | 57 | 27 |
| 13 | CH$_2$=CHCOO | 45 | 89 |
| 14 | OCH$_2$CH$_2$O | 59 | 0 |
| 15[d] | MeO | 21 | 35 |
| 16[e] | AcO | >95 | 97 |
| 17[e] | MeO | 90 | 13 |

[a]NMR yields determined using an internal standard.
[b]Enantiomeric excesses were determined by SFC on chiral stationary phase.
[c]No zinc salt was used.
[d]3.95 equiv of EtMgBr in Et$_2$O was used.
[e]4.5 equiv of EtMgCl was used.

It was observed that the method for preparing diorganozinc is technically simple, easy and fast. A simple manual or mechanical stirring of the reaction during the preparation of the organozinc compounds can be made (see FIG. 1). Filtration or centrifugation can also be used so as to led to a salt-free diorganozinc solution. Although similar results in terms of purity of the diorganozinc formed can be obtained using either technique, each offers certain advantages. While centrifugation is quick and allows the simultaneous treatment of several samples, filtration, on the other hand, allows a better recovering of the solution and works well on a large scale.

Since Zn(OMe)$_2$ was not so far commercially available, it can be prepared from Et$_2$Zn and MeOH.[ix] To bridge this experimental gap, an alternate convenient protocol was developed to generate this salt in situ (Equation 4). The latter was formed from ZnCl$_2$ and NaOMe (or KOMe). The resulting salt mixture can be used as a surrogate to pure Zn(OMe)$_2$ and is suitable for the diorganozinc preparation.

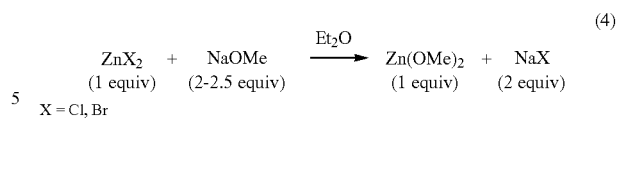

(4)

ZnX$_2$ + NaOMe →(Et$_2$O) Zn(OMe)$_2$ + NaX
(1 equiv) (2-2.5 equiv)   (1 equiv)   (2 equiv)
X = Cl, Br When compared to the addition of neat Et$_2$Zn, the use of Zn(OMe)$_2$, either isolated or generated in situ, produced excellent yields and selectivities (Table 2, entries 1-3). In a similar fashion, the addition of more functionalized zinc salts was just as successful, suggesting that their purity was equally excellent.

TABLE 2

Catalytic enantioselective addition to imines

Zn(OMe)$_2$ + RMgCl in Et$_2$O
(2 equiv)    (3.95 equiv)

↓ Et$_2$O

[R$_2$Zn + Mg salt(s) ↓]

↓ Centrifugation or filtration

R$_2$Zn in Et$_2$O
(R,R)-Me-BozPHOS™ (5 mol %)
Cu(OTf)$_2$ (10 mol %)
Toluene, 0° C., 16 h

| Entry | R | Yield [%][a] | ee [%][b] |
|---|---|---|---|
| 1 | Et | 95 | 98 |
| 2 | Et[c] | 90 | 98 |
| 3 | Et[d] | 96 | 98 |
| 4[e] | n-C$_{10}$H$_{21}$ | 73 | 97 |
| 5 | (dioxolane-alkyl structure) | n.d. | n.d. |
| 6 | n-Bu | 96 | 96 |
| 7 | i-Pr | 57 | 95 |

[a]Isolated yields.
[b]Enantiomeric excesses were determined by SFC on chiral stationary phase.
[c]Zn(OMe)$_2$ (2 equiv) was formed in situ from ZnCl$_2$ (2 equiv) and NaOMe (4.2 equiv).
[d]Neat Et$_2$Zn was dissolved in Et$_2$O.
[e]The reaction was run for 48 h.

As it can be seen in Schemes 1 and 2, further examples of catalytic enantioselective addition to imines was made. In these two examples the reaction was carried out by preparing and using a mixed diorganozinc (R$^2$ZnR$^3$) and more particularly n-C$_{10}$H$_{21}$ZnCH$_2$TMS and BnZnMe.

Scheme 1. Catalytic enantioselective addition to imines using mixed diorganozinc

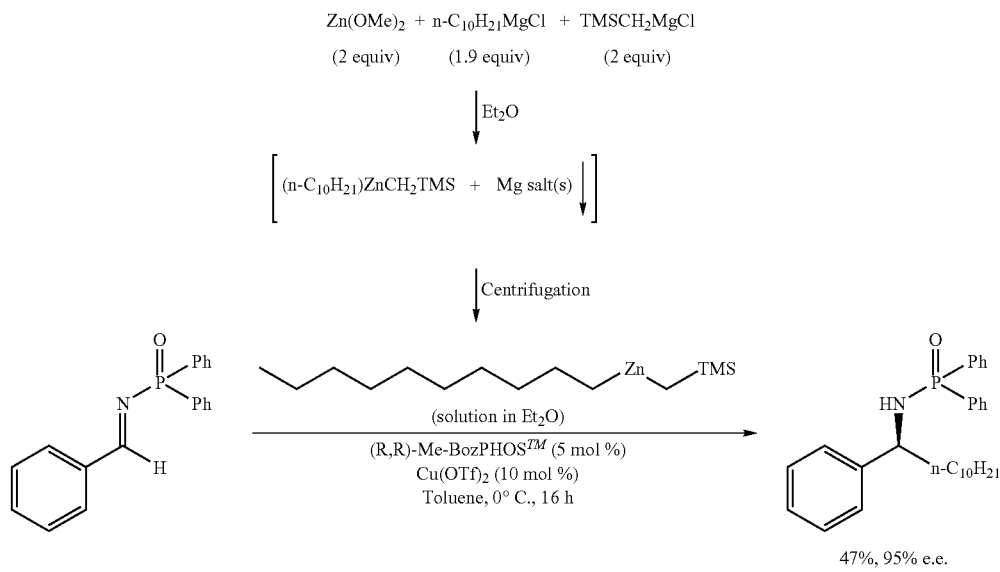

Scheme 2. Catalytic enantioselective addition to imines using mixed diorganozinc

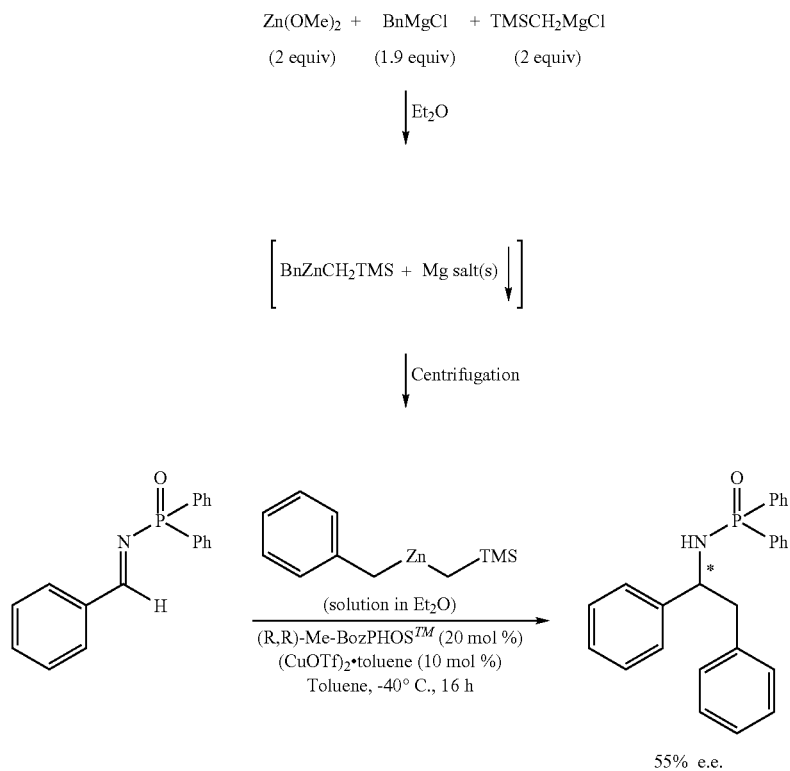

To prove the generality of such a methodology, various enantioselective addition systems were tested: the addition to β-nitroalkenes, to cyclohexenones and to aldehydes. Results obtained for the addition to β-nitroalkenes[x] turned out to be similar to the previous ones (Table 3).

TABLE 3

Catalytic enantioselective addition to β-nitroalkenes

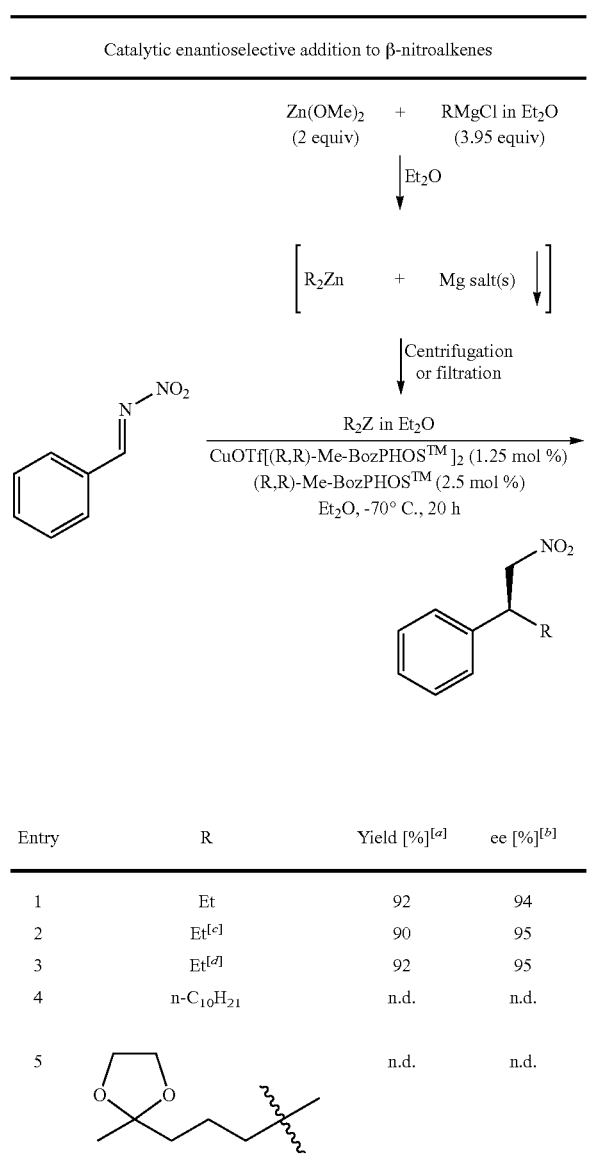

| Entry | R | Yield [%][a] | ee [%][b] |
|---|---|---|---|
| 1 | Et | 92 | 94 |
| 2 | Et[c] | 90 | 95 |
| 3 | Et[d] | 92 | 95 |
| 4 | n-C$_{10}$H$_{21}$ | n.d. | n.d. |
| 5 | (dioxolane structure) | n.d. | n.d. |

[a]Isolated yields.
[b]Enantiomeric excesses were determined by GC on chiral stationary phase.
[c]Zn(OMe)$_2$ (2 equiv) was formed in situ from ZnCl$_2$ (2 equiv) and NaOMe (4.2 equiv). ZnBr$_2$ was also used instead of ZnCl$_2$ and similar results were obtained.
[d]Neat Et$_2$Zn was dissolved in Et$_2$O.

The conjugated catalytic addition to cyclohexenone[xi] also proceeded smoothly with excellent reactivity. As the data indicate in Table 4, the synthesis of dialkylzinc reagents from Zn(OMe)$_2$ tolerated primary, secondary, branched, linear or long chains. Furthermore, functionalities are well tolerated insofar as Grignard reagents themselves are compatible with them.

TABLE 4

Catalytic enantioselective conjugated addition to cyclohexenone

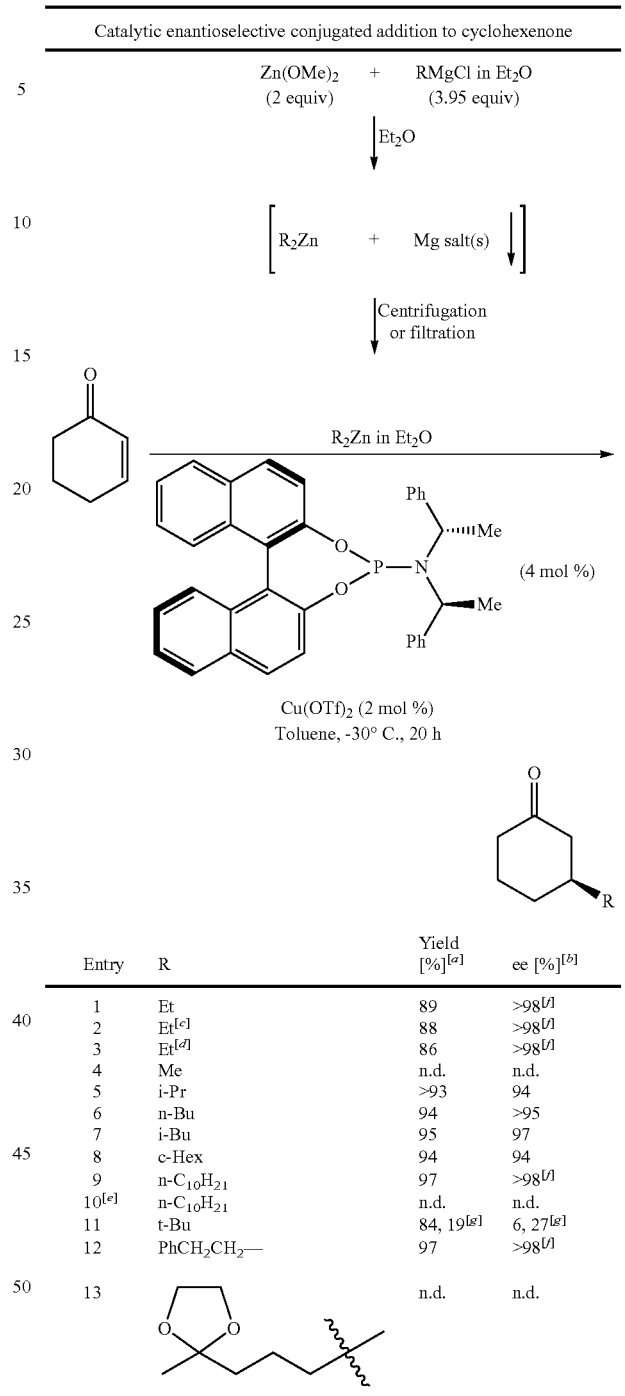

| Entry | R | Yield [%][a] | ee [%][b] |
|---|---|---|---|
| 1 | Et | 89 | >98[f] |
| 2 | Et[c] | 88 | >98[f] |
| 3 | Et[d] | 86 | >98[f] |
| 4 | Me | n.d. | n.d. |
| 5 | i-Pr | >93 | 94 |
| 6 | n-Bu | 94 | >95 |
| 7 | i-Bu | 95 | 97 |
| 8 | c-Hex | 94 | 94 |
| 9 | n-C$_{10}$H$_{21}$ | 97 | >98[f] |
| 10[e] | n-C$_{10}$H$_{21}$ | n.d. | n.d. |
| 11 | t-Bu | 84, 19[g] | 6, 27[g] |
| 12 | PhCH$_2$CH$_2$— | 97 | >98[f] |
| 13 | (dioxolane structure) | n.d. | n.d. |

[a]Isolated yield.
[b]Enantiomeric excesses were determined by SFC on chiral stationary phase or by $^{13}$C NMR spectroscopy after derivatization with 1,2-diphenyl ethylenediamine.
[c]Zn(OMe)$_2$ (2 equiv) was formed in situ from ZnCl$_2$ (2 equiv) and NaOMe (4.2 equiv).
[d]Neat R$_2$Zn was dissolved in Et$_2$O.
[e]Zn(C$_{10}$H$_{21}$)$_2$ was generated by hydroboration according to reference [3].
[f]The minor enantiomer could not be detected.
[g]1.0 equivalent of styrene has been added.

Further study of the reactivity of dialkylzinc reagents prepared with the method, reactions catalyzed by chiral amino alcohols have been tested.[xii] Once again, results of Table 5 showed that the enantioselective addition to aldehydes was very successful.

TABLE 5

Catalytic enantioselective addition to aldehydes

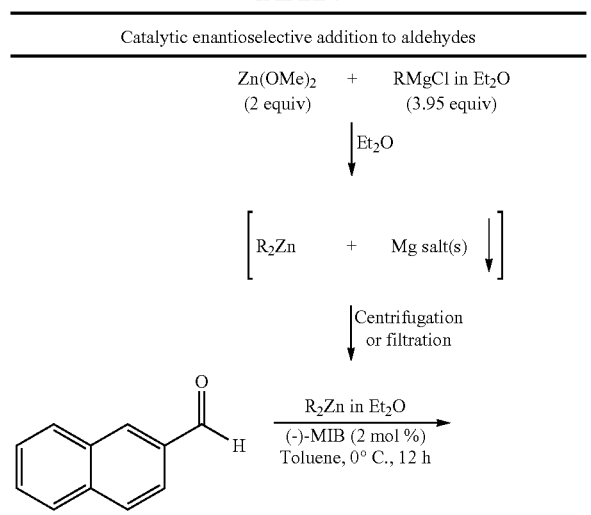

| Entry | R | Yield [%][a] | ee [%][b] |
|---|---|---|---|
| 1 | Et | 93 | 98 |
| 2 | Et[c] | 95 | 98 |
| 3 | Et[d] | 96 | 97 |
| 4 | n-C$_{10}$H$_{21}$ | 63[e] | 97 |
| 5 | 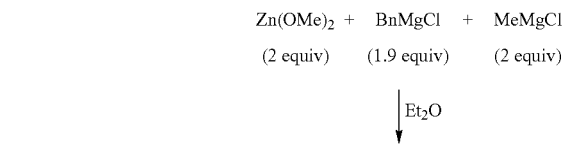 | n.d. | n.d. |

[a]Isolated yields.
[b]Enantiomeric excesses were determined by SFC on chiral stationary phase.
[c]Zn(OMe)$_2$ (2 equiv) was formed in situ from ZnCl$_2$ (2 equiv) and NaOMe (4.2 equiv).
[d]Neat Et$_2$Zn was dissolved in Et$_2$O.
[e]The low yield is explained by the formation of the reduction product.

Moreover, the synthesis of mixed diorganozinc reagents was found to be very simple: two different Grignard reagents can be added to Zn(OMe)$_2$ (entries 4-5)[xiii]

A further example of addition to an aldehyde is shown in Scheme 3. In this particular example, a mixed diorganozinc (R$^2$ZnR$^3$) was prepared and used.

Scheme 3. Catalytic enantioselective addition to aldehydes using mixed diorganozinc

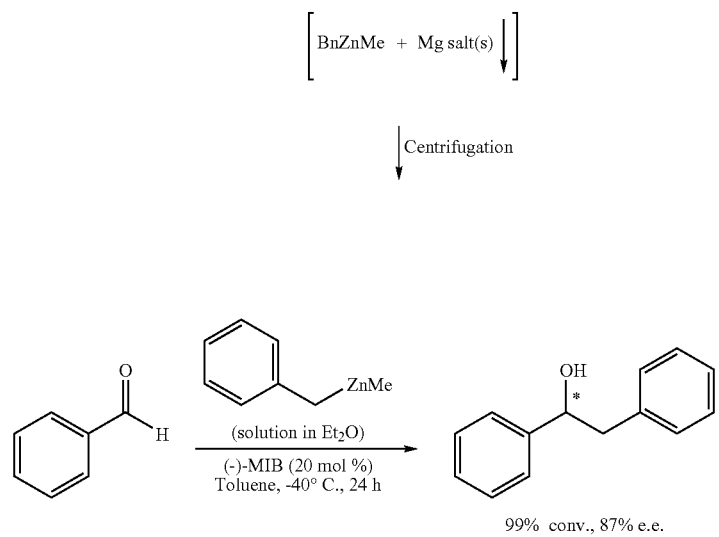

99% conv., 87% e.e.

Some other examples involving arylmagnesium reagents have also been made as shown in Table 6.

TABLE 6

Modification using brominated Grignard reagents $$Zn(OMe)_2 \;(2\text{ equiv}) \;+\; RMgBr \;(3.9\text{ equiv}) \;+\; NaOMe \;(4.8\text{ equiv})$$

$$\downarrow Et_2O$$

$$[\, R_2Zn \;+\; Mg\text{ salt(s)}\downarrow \;+\; NaBr\downarrow \,]$$

$$\downarrow \text{Centrifugation or filtration}$$

2-naphthaldehyde + $R_2Zn$ in $Et_2O$, (-)-MIB (5 mol %), Toluene, 0° C., 24 h → 1-(naphthalen-2-yl)alkan-1-ol

| Entry | R | Yield [%][a] | ee [%][b] |
| --- | --- | --- | --- |
| 1 | Et | 96 | 98 |
| 2 | Et[c] | 92 | 98 |
| 3 | Ph | 90 | 98 |
| 4[d],[e] | Ph | 98 | 98 |
| 5[d],[f] | Ph | 63 | 98 |
| 6 | TBDMSO(CH$_2$)$_4$ | 70 | 98 |

[a]Isolated yield.

[b]Enantiomeric excesses were determined by SFC on chiral stationary phase.

[c]EtMgBr (3.3 equiv) was used in combination with NaOBz (0.6 equiv).

[d]Mixed diorganozinc was used.

[d]EtZnPh was genereated from EtMgBr (1.5 equiv) and PhMgBr (1.45 equiv).

[e]EtZnPh was generated from Et$_2$Zn (0.75 equiv) and Ph$_2$Zn (0.75 equiv).

[f]EtZnPh was generated from EtMgBr (1.5 equiv), PhMgBr (1.45 equiv), ZnCl$_2$ (1.5 equiv) and 1,4-dioxane (10.5 equiv) (see reference [xi]).

Since a slight excess of Zn(OMe)$_2$ can be, for example, used in proportion to two equivalents of the Grigrard reagent (i.e. 1.0 equivalent of Zn(OMe)$_2$ for 1.95 equivalents of the Grignard reagent, which equals 1.02 equivalent of Zn(OMe)$_2$ for 2.0 equivalents of the Grignard reagent), traces of RZnOMe can still remain in the solution. However, such species are known to generate a stable tetramere, creating little or no interactions with catalytic systems, as illustrated herein. When necessary, the use of an excess of Grignard reagent in combination with an insoluble and slow to react scavenger such as NaOBz,[xiv] will eliminate the presence of organozinc alkoxide (Table 6, entry 2).

Some other examples involving cyclohexylmagnesium chloride have also been made as shown in Table 7.

TABLE 7

Other Examples using a Grignard reagent

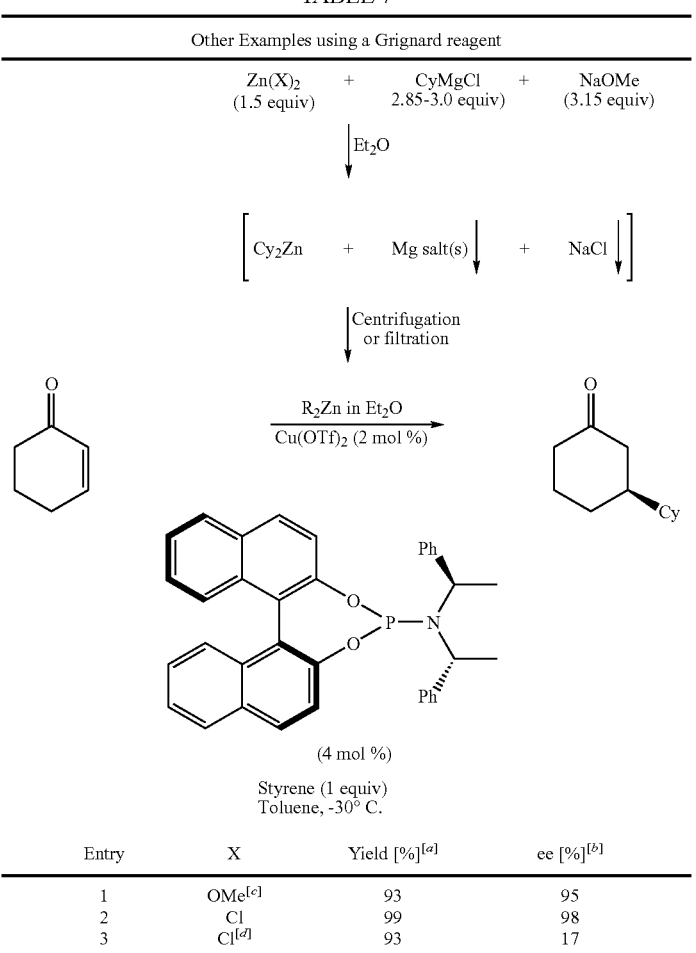

| Entry | X | Yield [%][a] | ee [%][b] |
|---|---|---|---|
| 1 | OMe[c] | 93 | 95 |
| 2 | Cl | 99 | 98 |
| 3 | Cl[d] | 93 | 17 |

[a]GC yield or ¹H NMR yield.
[b]Enantiomeric excesses were determined by GC on chiral stationary phase.
[c]0 equivalent of NaOMe was added.
[d]Order of addition changed: NaOMe added to ZnCl₂, then CyMgCl added.

Some examples of substantially salt-free diorganozinc compositions have been prepared.

TABLE 8

Preparation of substantially salt-free diorganozinc compounds $$R_2Zn \cdot MgX_2 \xrightarrow[\text{2. [-XMgOMe]}]{\text{1. NaOMe}} R_2Zn$$

| Entry | R | X | Method of Separation | Yield [%][a] |
|---|---|---|---|---|
| 1 | Cy | Cl | Centrifugation | 57[b] |
| 2 | Cy | Cl | Filtration | 92 |

[a]Yield obtained by titration with iodine.
[b]Centrifuged solids not extracted to increase the yield.

In summary, the low solubility of magnesium salts such as magnesium methoxide has been exploited in order to synthesize diorganozinc reagents dissolved in a ethereal solvent (such as diethylether, t-butylmethylether, dibutylether, diphenylether, diisopropylether, dipropylether, dipentylether, dimethoxymethane, cyclopentylmethylether, diethoxymethane, derivatives or analogues thereof) without unwanted reaction by-products. It represents an attractive method to access both highly functionalized dialkylzinc and diarylzinc reagents. It also permits to easily prepare diorganozinc compounds. Finally, such a method shows no change in the reactivity of all tested asymmetric catalytic reactions in comparison to purified reagents.

In Tables 1 to 8 and Schemes 1 to 3 the expression "Mg salts(s)" refers to a precipitate that comprises at least one magnesium salt chosen from $Mg(OMe)_2$, $MgX(OMe)$, $MgX_2$, and mixtures thereof, wherein X is Cl, Br, or I in accordance with the type of Grignard reagent used i.e. chlorinated, brominated, or iodinated.

EXAMPLES

Typical experimental procedure: $R_2Zn$ synthesis from $Zn(OMe)_2$ and RMgCl: To a test tube (18×100 mm) equipped with a magnetic stirrer (under argon atmosphere) charged with $Zn(OMe)_2$ (637 mg, 5 mmol) was added anhydrous $Et_2O$ (5 mL) at room temperature. The heterogeneous solution was stirred for 5-15 min and cooled to 0° C. for another 5-15 min. RMgCl 2M in $Et_2O$ (9.75 mmol) was added dropwise with vigorous stirring over 5-10 min at 0° C., and the heterogeneous solution was allowed to stir at room temperature for 1 h. The mixture was then centrifuged for 5-15 min (or filtered) and the $R_2Zn$ solution (4.5 M)[xv],[xvi] was gently transferred via cannula into an empty flame-dried flask purged with argon (or added to a reaction mixture via syringe). Results obtained using such a procedure can be found, for example, in Tables 2 to 5.

Typical experimental procedure: $R_2Zn$ synthesis from $ZnCl_2$, NaOMe and RMgCl: To a test tube (18×100 mm) equipped with a magnetic stirrer (under argon atmosphere) charged with $ZnCl_2$ (682 mg, 5 mmol) and NaOMe (567 mg, 10.5 mmol) was added anhydrous $Et_2O$ (5 mL) at room temperature (exothermic). The heterogeneous solution was stirred for 20 min and cooled to 0° C. for another 5-15 min. RMgCl 2M in $Et_2O$ (9.75 mmol) was added dropwise with vigorous stirring over 5-10 min at 0° C., and the heterogeneous solution was allowed to stir at room temperature for 2 h. The mixture was then centrifuged for 5-15 min (or filtered) and the $R_2Zn$ solution (≈0.5 M) was gently transferred via cannula into an empty flame-dried flask purged with argon (or added to a reaction mixture via syringe). Results obtained using such a procedure (using $ZnCl_2$ to prepare $Zn(OMe)_2$ in situ) can be found, for example, in some entries of Tables 2 to 5.

Another typical experimental procedure: $R_2Zn$ synthesis from $ZnCl_2$, NaOMe and RMgCl: To a 100 mL flask equipped with a magnetic stirrer (under argon atmosphere) charged with $ZnCl_2$ (1.31 g, 9.6 mmol) was added anhydrous $Et_2O$ (10 mL) at room temperature. The heterogeneous solution was stirred for 2 hours and cooled to 0° C. for another 5-15 min. RMgCl 2M in $Et_2O$ (18.7 mmol) was added dropwise with vigorous stirring over 30 min at 0° C., and the heterogeneous solution was allowed to stir at room temperature for 2 h. NaOMe (1.09 g, 20.2 mmol) was then added and the mixture was stirred for 20 hours. The mixture was then centrifuged for 10 min (or filtered) and the $R_2Zn$ solution (≈0.4 M) was gently transferred via cannula into an empty flame-dried flask purged with argon (or added to a reaction mixture via syringe). Results obtained using such a procedure can be found, for example, in Table 7.

Typical experimental procedure with $Zn(OMe)_2$, NaOMe and RMgBr: To a test tube (18×100 mm) equipped with a magnetic stirrer (under argon atmosphere) charged with $Zn(OMe)_2$ (637 mg, 5 mmol) and NaOMe (650 mg, 12 mmol) was added anhydrous $Et_2O$ (5 mL) at room temperature. The heterogeneous solution was stirred for 5-15 min and cooled to 0° C. for another 5-15 min. RMgBr 2M in $Et_2O$ (9.75 mmol) was added dropwise with vigorous stirring over 5-10 min at 0° C., and the heterogeneous solution was allowed to stir at room temperature for 2 h. The mixture was then centrifuged for 5-15 min (or filtered) and the $R_2Zn$ solution (≈0.5 M) was gently cannulated in an empty flame-dried flask purged with argon (or added to a reaction with a syringe). Results obtained using such a procedure can be found, for example, in Table 6.

Typical experimental procedure with mixed diorganozinc compounds ($R^2ZnR^3$): To a test tube (18×100 mm) equipped with a magnetic stirrer (under argon atmosphere) charged with $Zn(OMe)_2$ (637 mg, 5 mmol) was added anhydrous $Et_2O$ (5 mL) at room temperature. The heterogeneous solution was stirred for 5-15 min and cooled to 0° C. for another 5-15 min. $R^2MgCl$ 2M in $Et_2O$ (5.00 mmol) was added dropwise with vigorous stirring over 5-10 min at 0° C., then $R^3MgCl$ 2M in $Et_2O$ (4.75 mmol) was added dropwise with vigorous stirring over 5-10 min at 0° C. and the heterogeneous solution was allowed to stir at room temperature for 1 h. The mixture was then centrifuged for 5-15 min (or filtered) and the $R^2ZnR^3$ solution (≈0.5 M)[xvi] was gently transferred via cannula into an empty flame-dried flask purged with argon (or added to a reaction mixture via syringe). Results obtained using such a procedure can be found, for example, in Schemes 1 and 2 and in some entries of Table 6.

Typical experimental procedure for the preparation of substantially salt-free diorganozinc compounds: To a 100 mL flask equipped with a magnetic stirrer (under argon atmosphere) charged with a diorganozinc solution containing 2 equivalents of magnesium halide (9.6 mmol of $R_2Zn$ in 20 mL solvent such as diethylether, tert-butylmethylether, 2-methyltetrahydrofuran, or diethoxymethane, was added NaOMe (1.09 g, 20.2 mmol) and the mixture was stirred for 20 hours. The mixture was then centrifuged for 10 min (or filtered) and the $R_2Zn$ solution M) was gently transferred via cannula into an empty flame-dried flask purged with argon (or added to a reaction mixture via syringe). Obtention of a substantially salt-free $R_2Zn$ composition was proven indirectly by the enantioselective addition of $R_2Zn$ to 2-cyclohexen-1-one, which gave similar results (>90% ee) to entries 1-2 found in table 7 (presence of salts lower considerably the enantioselectivity of addition, for example, <50% ee). Results obtained in the preparation of a substantially salt-free composition of diorganozinc using such a procedure can be found, for example, in Table 8. It is possible to remove the solvent (for example by means of a distillation) so as to obtain the substantially salt-free diorganozinc compound in a neat form. It is also possible to concentrate the composition by removing at least a portion of solvent (distillation, evaporation, filtration membranes, etc.)

CHARACTERIZATION

Other than exceptional cases, compounds in Tables 1 to 7 and Scheme 1 were fully characterized (NMR $^1H$ and $^{13}C$, IR, mp, $[\alpha]_D$, MS, E.A, etc.). Exceptions are compounds obtained by addition of t-butyl and benzyl (Table 4, entry 11; Scheme 2 and 3), for which only NMR $^1H$ and GC/SFC data are available. For known compounds, obtained data are consistent with literature values.[xvii,xviii]. For new compounds (Table 2, entry 4; Scheme 1; Table 4, entry 9; Table 5, entry 4 and Table 6, entry 6) characterization values are consistent with proposed structures and are reported hereafter.

Dicyclohexylzinc (as a 0.41 M solution in diethyl ether): Absence of remaining alkylmagnesium reagent was confirmed by a negative Gilman test.[xix] Titer was determined by reaction with iodine dissolved in THF (containing LiCl, 0.5M).[xv] The solution given after titration was dissolved in TBME and washed with 1M HCl, dried with $Na_2SO_4$ and analysed by GC (area % of products): iodocyclohexane (89%), cyclohexane (6%), cyclohexanol (2%), cyclohexene (2%); Side products cyclohexanol and cyclohexene were not detected by $^1H$ and $^{13}C$ NMR. $^1H$ NMR (400 MHz, 1:1 v/v $Cy_2Zn/Et_2O:C_6D_6$) δ 0.96-1.06 (hidden under $Et_2O$ signal, identified by HMQC; m, $2H_{H-C-Zn}$), 1.32-1.50 (m, 6H), 1.55-1.64 (m, 6H), 1.65-1.81 (m, 8H); $Et_2O$ signals: 1.06 (t, J=7.2 Hz, 6H), 3.27 (q, J=7.2 Hz, 4H); cyclohexane signal: 1.36 (s, 12H, 14 mol % vs $Cy_2Zn$); $^{13}C$ NMR (100 MHz, 1:1 v/v $Cy_2Zn/Et_2O:C_6D_6$) δ 28.27 ($2CH_2$), 31.05 ($4CH_2$), 32.24 ($4CH_2$), 33.43 (2CH); $Et_2O$ signals: 15.38 ($2CH_3$), 65.88 ($2CH_2$); cyclohexane signal: 27.22 ($6CH_2$); $^1H$ NMR (400 MHz, 1:1 v/v $Cy_2Zn/Et_2O:CDCl_3$) δ 0.50-0.80 (hidden under $Et_2O$ signal; m, 0.85-0.99 (m, 6H), 1.05-1.14 (m, 6H), 1.15-1.25 (m, 4H), 1.26-1.35 (m, 4H); $Et_2O$ signals: 0.68 (t, J=7.2 Hz, 6H), 2.94 (q, J=7.2 Hz, 4H); cyclohexane signal: 0.95 (s, 12H, 14 mol % vs $Cy_2Zn$); $^{13}C$ NMR (100 MHz, 1:1 v/v $Cy_2Zn/Et_2O:CDCl_3$) δ 27.24 ($2CH_2$), 30.00 ($4CH_2$), 31.39 ($4CH_2$), 32.28 (2CH); $Et_2O$ signals: 14.30 ($2CH_3$), 64.95 ($2CH_2$); cyclohexane signal: 26.26 ($6CH_2$).

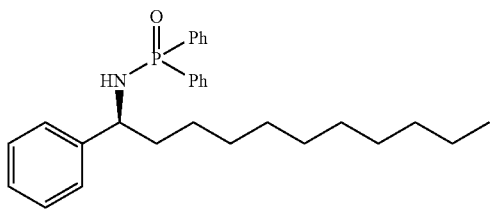 [SMILES: CCCCCCCCCC[C@H](NP(=O)(c1ccccc1)c1ccccc1)c1ccccc1]

P,P-diphenyl-N-[(1S)-1-phenylundecyl]phosphinic amide: mp 95-96° C.; $R_f$ 0.55 (10:90 hexane:EtOAc); $[\alpha]_D^{20}$ −6.0 (c 1.02, CHCl$_3$); $^1$H NMR (400 MHz, CDCl$_3$) δ 0.88 (t, J=6.9 Hz, 2H), 1.05-1.37 (m, 8H), 1.75-1.87 (m, 1H), 1.92-2.04 (m, 1H), 3.35 (dd, J=9.6, 6.5 Hz, 0H), 4.16 (qd, J=9.6, 6.5 Hz, 1H), 7.17 (dd, J=7.0, 1.3 Hz, 1H), 7.20-7.35 (m, 3H), 7.37-7.51 (m, 2H), 7.76 (ddd, J=11.9, 8.2, 1.1 Hz, 1H), 7.87 (ddd, J=11.8, 8.1, 1.2 Hz, 1H); $^{13}$C NMR (100 MHz, CDCl$_3$) δ 13.7, 22.3, 25.7, 28.9, 29.0, 29.0, 29.2 (2C), 31.5, 39.4 (d, $J_{C-P}$=3.8 Hz), 55.5, 126.1, 126.6, 127.8 (d, $J_{C-P}$=12.7 Hz), 128.0 (d, $J_{C-P}$=12.5 Hz), 128.1, 131.2 (d, $J_{C-P}$=2.7 Hz), 131.4 (d, $J_{C-P}$=2.7 Hz), 131.5 (d, $J_{C-P}$=9.8 Hz), 132.2 (d, $J_{C-P}$=9.8 Hz), 131.8 (d, $J_{C-P}$=121.9 Hz), 133.7 (d, $J_{C-P}$=120.7 Hz), 143.6 (d, $J_{C-P}$=6 Hz); $^{31}$P NMR (162 MHz, CDCl$_3$) δ 22.78; HRMS m/z (APCI+) calcd for C$_{29}$H$_{39}$N OP [M+H]$^+$: 448.27693; found: 448.2770; IR (neat) 3147, 2923, 2853, 1457, 1438, 1197, 1181, 1108, 1068, 932, 750, 720, 693, 605 cm$^{-1}$.

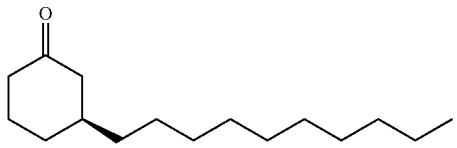 [SMILES: CCCCCCCCCC[C@H]1CCCC(=O)C1]

(3S)-3-decylcyclohexanone: $R_f$ 0.51 (90:10 n-hexane:EtOAc); $[\alpha]_D^{20}$ −12.1 (c 1.08, CHCl$_3$); $^1$H NMR (400 MHz, CDCl$_3$) δ 0.83 (t, J=6.9 Hz, 3H), 1.13-1.35 (m, 19H), 1.52-1.65 (m, 1H), 1.71 (s, 1H), 1.80-1.89 (m, 1H), 1.90-2.04 (m, 2H), 2.14-2.24 (m, 1H), 2.28 (dd, J=10.4, 7.0 Hz, 1H), 2.33-2.40 (m, 1H); $^{13}$C NMR (100 MHz, CDCl$_3$) δ 14.1, 22.7, 25.4, 26.7, 29.4, 29.7 (2C), 29.7, 29.8, 31.4, 32.0, 36.7, 39.2, 41.5, 48.3, 211.7; HRMS m/z (APCI+) calcd for C$_{16}$H$_{31}$O [M+H]$^+$: 239.23694; found: 239.23696; IR (neat) 2922, 2852, 1714, 1465, 1345, 1313, 1224, 815, 722, 630 cm$^{-1}$.

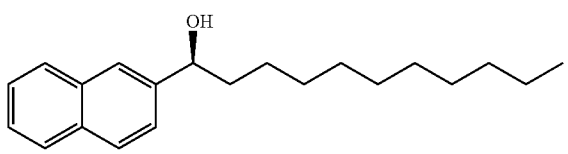 [SMILES: CCCCCCCCCC[C@H](O)c1ccc2ccccc2c1]

(1S)-1-(2-naphthyl)-1-undecanol: mp 53-54° C.; $R_f$ 0.35 (20:80 EtOAc:hexane); $[\alpha]_D^{20}$ −23.0 (c 1.08 CHCl$_3$); $^1$H NMR (400 Hz, CDCl$_3$) δ 0.96 (t, J=6.8 Hz, 3H), 1.32 (s, 15H), 1.45 (d, J=8.7 Hz, 1H), 1.97-1.74 (m, 2H), 2.46 (s, 1H), 4.81 (t, J=6.6 Hz, 1H), 7.57-7.46 (m, 3H), 7.77 (s, 1H), 7.92-7.81 (m, 3H); $^{13}$C NMR (100 MHz, CDCl$_3$) δ 14.3, 22.9, 26.0, 29.5, 29.7 (2C), 29.8 (2C), 32.1, 39.1, 74.9, 124.3, 124.8, 125.9, 126.2, 127.8, 128.1, 128.3, 133.1, 133.4, 142.5; HRMS m/z (APCI+) calcd for C$_{21}$H$_{30}$NaO [M+Na]$^+$: 321.21888; found: 321.21787; IR (neat) 3273, 3054, 2919, 2850, 1507, 1465, 1313, 1065, 1031, 896, 860, 826, 748 cm$^{-1}$.

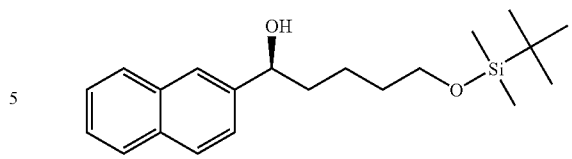

(1S)-5-{[tert-butyl(dimethyl)silyl]oxy}-1-(2-naphthyl)-1-pentanol: $R_f$ 0.25 (20:80 EtOAc:hexane); $[\alpha]_D^{20}$ −19.5 (c 1.04 CHCl$_3$); $^1$H NMR (400 MHz, CDCl$_3$) δ 0.02 (s, 6H), 0.87 (s, 9H), 1.29-1.40 (m, 1H), 1.42-1.51 (m, 1H), 1.55 (qn, J=6.9 Hz 2H), 1.75-1.94 (m, 2H), 2.17 (d, J=3.1 Hz, 1H), 3.58 (t, J=6.4 Hz, 2H), 4.81 (td, J=6.7, 2.9 Hz, 1H), 7.40-7.51 (m, 3H), 7.75 (s, 1H), 7.77-7.87 (m, 3H); $^{13}$C NMR (100 MHz, CDCl$_3$) δ−5.1, 18.5, 22.3, 26.2, 32.8, 38.9, 63.3, 74.9, 124.3, 124.8, 125.9, 126.3, 127.9, 128.1, 128.4, 133.2, 133.5, 142.4; HRMS m/z (APCI+) calcd for C$_{21}$H$_{32}$NaO$_2$Si [M+Na]$^+$: 367.20638; found: 367.20512; IR (neat) 3351, 3055, 2928, 2856, 1602, 1508, 1471, 1462, 1387, 1360, 1254, 1096, 835, 775, 746, 662 cm$^{-1}$.

REFERENCES

[i] a) K. Soai, T. Kawasaki in *The chemistry of Organozinc Compounds* (Eds.: Z. Rappoport, I. Marek), WILEY, Chichester, 2006, pp. 555-593; b) K. Soai, S. Niwa, *Chem. Rev.* 1992, 92, 833-856; c) L. Pu, H.-B. Yu, *Chem. Rev.* 2001, 101, 757-824; d) R. Bloch, *Chem. Rev.* 1998, 98, 1407-1438; e) E. A. Bercot, T. Rovis, *J. Am. Chem. Soc.* 2004, 126, 10248-10249; f) F. Schmidt, R. T. Stemmler, J. Rudolph, C. Bolm, *Chem. Soc. Rev.* 2006, 35, 454-470.

[ii] a) P. Knochel, R. D. Singer, Chem. Rev. 1993, 93, 2117-2188; b) P. Knochel, H. Leuser, L.-Z. Gong, S. Perrone, F. F. Kneisel in The chemistry of Organozinc Compounds (Eds.: Z. Rappoport, I. Marek), Wiley, Chichester, 2006, pp. 287-393; c) P. Knochel, H. Leuser, L.-Z. Gong, S. Perrone, F. F. Kneisel in Handbook of Functionalized Organometallics (Ed.: P. Knochel), Wiley-VCH, Weinheim, 2005, chapter 7; d) P. Knochel, N. Millot, A. Rodriguez, C. E. Tucker, Org. React. 2001, 58, 417-731; e) C. Bolm, J. Rudolph, J. Am. Chem. Soc. 2002, 124, 14850-14851.

[iii] a) M. Kitamura, T. Miki, K. Nakano, R. Noyori, *Bull. Chem. Soc. Jpn* 2000, 73, 999-1014; b) J. Rudolph, M. Lormann, C. Bolm, S. Dahmen, *Adv. Synth. Catal.* 2005, 347, 1361-1368; c) S.-J. Jeon, H. Li, C. García, L. K. LaRochelle, P. J. Walsh, *J. Org. Chem.* 2005, 70, 448-455.

[iv] Even if MgCl$_2$ and LiCl are hardly soluble in Et$_2$O.

[v] a) Boron residues significantly decreased yields when used in catalytic addition to imines (Unpublished results); b) For an example of the detrimental effect of boron residues on selectivities: N. A. Powell, S. D. Rychnovsky, *J. Org. Chem.* 1999, 64, 2026-2037.

[vi] The presence of residual Et$_2$Zn or iPr$_2$Zn from a Zn-halogen exchange generally leads to the undesired addition of Et or iPr group.

[vii] a) A. Guijarro *The Chemistry of Organozinc Compounds* (Eds.: Z. Rappoport, I. Marek), WILEY, Chichester, 2006, pp. 193-236; b) R. M. Fabicon, H. G. Richey, Jr., *J. Chem. Soc. Dalton Trans.* 2001, 783-788.

[viii] a) A. A. Boezio, J. Pytkowicz, A. Cote, A. B. Charette, *J. Am. Chem. Soc.* 2003, 125, 14260-14261; b) A. Côté, A. A. Boezio, A. B. Charette, *Proc. Natl Acad. Sci. USA* 2004, 101, 5405-5410; c) A. B. Charette, A. A. Boezio, A. Côté, E. Moreau, J. Pytkowicz, J.-N. Desrosiers, C. Legault, *Pure Appl. Chem.* 2005, 77, 1259-1267.

[ix] a) G. E. Coates, D. Ridley, *J. Chem. Soc.* 1965, 1870-1877; b) C. L. Carnes, K. J. Klabunde *Langmuir* 2000, 16, 3764-3772.

[x] A. Côté, V. N. G. Lindsay, A. B. Charette, *Org. Lett.* 2007, 9, 85-87.

[xi] a) B. L. Feringa, M. Pineschi, L. A. Arnold, R. Imbos, A. H. M. de Vries, *Angew. Chem.* 1997, 109, 2733-2736; *Angew. Chem. Int. Ed Engl.* 1997, 36, 2620-2623; b) K. Li, A. Alexakis, *Angew. Chem.* 2006, 118, 7762-7765; *Angew. Chem. Int. Ed* 2006, 45, 7600-7603.

[xii] W. A. Nugent, *Chem. Commun.* 1999, 1369-1370.

[xiii] Dialkylzinc: a) C. Lutz, P. Jones, P. Knochel, *Synthesis* 1999, 312-316; b) S. Berger, F. Langer, C. Lutz, P. Knochel, T. A. Mobley, C. K. Reddy, *Angew. Chem.* 1997, 109, 1603-1605; *Angew. Chem. Int. Ed. Engl.* 1997, 36, 1496-1498; c) C. Lutz, P. Knochel, *J. Org. Chem.* 1997, 62, 7895-7898; d) P. Jones, P. Knochel, *J. Chem. Soc. Perkin Trans. I* 1997, 3117-3118; e) B. H. Lipshutz, R. W. Vivian, *Tetrahedron Lett.* 1999, 40 2871-2874; f) B. H Lipshutz, M. R. Wood, R. Tirado, *J. Am. Chem. Soc.* 1995, 117, 6126-6127; g) A. Rimkus, N. Sewald, *Org. Lett.* 2002, 4, 3289-3291; Alkylalkenylzinc: h) S. Dahmen, S. Bräse, *Org. Lett.* 2001, 3, 4119-4122; i) P. Wipf, W. Xu *Tetrahedron Lett.* 1994, 35, 5197-5200; j) W. Oppolzer, R. N. Radinov, E. El-Sayed, *J. Org. Chem.* 2001, 66, 4766-4770; k) S.-J. Jeon, Y. K. Chen, P. J. Walsh, *Org. Lett.* 2005, 7, 1729-1732; Alkylarylzinc: l) C. Bolm, N. Hermanns, J. P. Hildebrand, K. Muñiz, *Angew. Chem.* 2000, 112, 3607-3609; *Angew. Chem. Int. Ed* 2000, 39, 3465-3467; m) J. Rudolph, T. Rasmussen, C. Bolm, P.-O, Norrby, *Angew. Chem.* 2003, 115, 3110-3113; *Angew. Chem. Int. Ed* 2003, 42, 3002-3005; Alkylakynylzinc: n) S. Niwa, K. Soai, *J. Chem. Soc. Perkin Trans I* 1990, 937-943.

[xiv] In most cases, $CH_3CO_2Na$ and $CF_3CO_2Na$ also afford good results.

[xv] For a more precise concentration: A. Krasovskiy, P. Knochel, *Synthesis,* 2006, 890-891.

[xvi] The volume of the recovered solution is dependent on the nature of the Grignard reagent. For example, 6 mL of $Et_2Zn$ solution (0.5M) was obtained with EtMgCl.

[xvii] For more details about the characterization data, see: A. Me, A. B. Charette, *J. Am. Chem. Soc.* 2008, 130, 2771-2773.

[xviii] a) A. A. Boezio, J. Pytkowicz, A. Côté, A. B. Charette, *J. Am. Chem. Soc.* 2003, 125, 14260-14261; b) T. Suzuki, T. Shibata, K. Soai, *J. Chem. Soc., Perkin Trans I* 1997, 2757-2760; c) H.-L. Zhang, X.-M. Zhang, L.-Z. Gong, A.-Q. Mi, X. Cui, Y.-Z. Jiang, M. C. K. Choi, A. S. C. Chan, *Org. Lett.* 2002, 4, 1399-1402; d) B.-M. Park, S. Mun, J. Yun, *Adv. Synth. Catal.* 2006, 348, 1029-1032; e) X.-M. Zhang, H.-L. Zhang, W.-Q. Lin, L.-Z. Gong, A.-Q. Mi, X. Cui, Y.-Z. Jiang, K.-B. Yu, *J. Org. Chem.* 2003, 68, 4322-4329; f) A. Alexakis, C. Benhaim, S. Rosset, M. Humman, *J. Am. Chem. Soc.* 2002, 124, 5262-5263; g) M.-C. Wang, C.-L. Xu, F. Cheng, X. Ding, *Tetrahedron* 2006, 62, 12220-12226; h) J.-N. Desrosiers, A. Cote, A. A. Boezio, A. B. Charette, *Org. Synth.* 2006, 83, 5-17; i) K. Soai, T. Hatanaka, T. Miyazawa, *Chem. Commun.* 1992, 1097; j) H.-L. Zhang, X. M. Zhang, L. Z. Gong, A. Q. Mi, X. Cui, Y. Z. Jiang, M. C. K. Choi, A. S. C. Chan, *Org. Lett.* 2002, 4, 1399; k) P. G. Andersson, D. Guijarro, D. Tanner, *J. Org. Chem.* 1997, 62, 7364; l) P. Pinho, P. G. Andersson, *Tetrahedron* 2001, 57, 1615; m) T. Suzuki, Y. Hirokawa, K. Ohtake, T. Shibata, K. Soai, *Tetrahedron: Asymmetry* 1997, 8, 4033; n) D. Guijarro, P. Pinho, P. G. Andersson, *J. Org. Chem.* 1998, 63, 2530; o) T. Suzuki, T. Shibata, K. Soai, *J. Chem. Soc., Perkin Trans I* 1997, 2757; p) X. M. Zhang, L. H. Gong, A. Q. Mi, X. Cui, Y. H. Jiang, M. C. K. Choi, A. S. C. Chan, *Tetrahedron Lett.* 2001, 42, 6369-6372. q) I. Sato, R. Kodaka, K. Soai, *J. Chem. Soc., Perkin Trans I* 2001, 2912; r) C. Jimeno, A. Vidal-Ferran, A. Moyano, M. A. Pericas, A. Riera, *Tetrahedron Lett.* 1999, 40, 777; s) K. Soai, T. Suzuki, T. Shono, *Chem. Commun.* 1994, 317; t) I. Sato, R. Kodaka, K. Soai, *J. Chem. Soc., Perkin Trans. I* 2001, 2912; u) W. Buchowiecki, Z. Grosman-Zjawiona, J. Zjawiony, *Tetrahedron Lett.* 1985, 26, 1245-1248; v) S. Degrado, H. Mizutani, A. H. Hoveyda, *J. Am. Chem. Soc.* 2001, 123, 755-756; w) J. B. Tuttle, S. G. Ouellet, D. W. C. MacMillan, *J. Am. Chem. Soc.* 2006, 128, 12662-12663; x) E. L. Stangeland, T. Sammakia, *Tetrahedron* 1997, 53, 16503-16510; y) Q.-L. Zhou, A. Pfaltz, *Tetrahedron* 1994, 50, 4467-4478; z) E. J. Corey, R. Naef, F. J. Hannon, *J. Am. Chem. Soc.* 1986, 108, 7114-7116; aa) N. J. A. Martin, B. List, *J. Am. Chem. Soc.* 2006, 128, 13368-13369; ab) M. Kanai, Y. Nakagawa, K. Tomioka, *Tetrahedron* 1999, 55, 3843-3854; ac) M. J. Totleben, D. P. Curran, P. Wipf, *J. Org. Chem.* 1992, 57, 1740-1744; (d) J.-Y. Liu, Y.-J. Jang, W.-W. Lin, J.-T. Liu, C.-F. Yao, *J. Org. Chem.* 2003, 68, 4030-4038; ae) P. Jones, C. K. Reddy, P. Knochel, *Tetrahedron* 1998, 54, 1471-1490; af) P. Wipf, W. Xu, J. H. Smitrovich, R. Lehmann, L. M. Venanzi, *Tetrahedron* 1994, 50, 1935-1954; ag) R. D. Rieke, W. R. Klein, T.-C. Wu, *J. Org. Chem.* 1993, 58, 2492-2500; ah) C. R. Graves, K. A. Scheidt, S. T. Nguyen, *Org. Lett.* 2006, 8, 1229-1232; ai) R. Almansa, D. Guijarro, M. Yus, *Tetrahedron* 2007, 63, 1167-1174; aj) H. Ohta, N. Kobayashi, K. Ozaki, *J. Org. Chem.* 1989, 54, 1802-1804; ak) D. M. Mampreian, A. H. Hoveyda, *Org. Lett.* 2004, 6, 2829-2832; al) H. Choi, Z. Hua, I. Ojima, *Org. Lett.* 2004, 6, 2689-2691.

[xix] a) H. Gilman, F. Schulze *J. Am. Chem. Soc.* 1925, 47, 2002-2005 b) H. Gilman, W. E. Catlin Org. Synth. 1926, 6, 22-25; *Organic Syntheses*; Wiley & Sons: New York, 1941; Collect. Vol. I, p. 188-191.

What is claimed is:

1. A method for preparing a compound of formula (I):

wherein
R is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl;

said method comprising reacting a compound of formula (II) with at least one compound chosen from compounds of formulas (IIIa), (IIIb), and (IIIc):

wherein
X is chosen from —OR$^1$, —SR$^1$, Cl, Br, C$_2$-C$_{20}$ alkylcarboxylate, C$_2$-C$_{12}$ heteroarylcarboxylate, and C$_6$-C$_{20}$ arylcarboxylate, and when X is Cl or Br, a compound of formula (VI) is further added;
R is as previously defined;
M is Na or K;
M$^1$ is Mg;
M$^2$ is Li, or Na;
T is F, Cl, Br, I, OSO$_2$R, CN, OR or OC(O)R;
R$^1$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl, or
said R$^1$ are linked together so as to form a 5 to 8 membered ring; and
R$^6$ is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_r$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl,
said alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, —OH, —CN, —NO$_2$, —SH, —OR, —SR, C$_1$-C$_6$ alkoxy, C$_1$-C$_8$ alkyl, C$_2$-C$_8$ alkenyl, C$_2$-C$_8$ alkynyl, C$_1$-C$_6$ aminoalkyl, C$_6$-C$_{20}$ aralkyl, C$_6$-C$_{12}$ aryl, C$_3$-C$_8$ cycloalkyl, C$_1$-C$_{12}$ heteroaryl, C$_1$-C$_{12}$ heterocyclyl, C$_2$-C$_{20}$ carboxylic acid ester, C$_3$-C$_{20}$ carboxylic acid amide, C$_1$-C$_6$ hydroxyalkyl, C$_2$-C$_3$ cyclic acetal, C$_1$-C$_{12}$ acetal, C$_1$-C$_{12}$ acyclic orthoester, C$_4$-C$_6$ cyclic orthoester, C$_1$-C$_{12}$ sulfone, C$_1$-C$_{12}$ sulfoxide, C$_2$-C$_{12}$ carbamate, C$_2$-C$_{12}$ urea, C$_2$-C$_{12}$ sulfonamide, C$_2$-C$_{12}$ sulfoxamide, C$_2$-C$_{12}$ phosphonate, C$_2$-C$_{12}$ phosphinoyl, C$_2$-C$_{12}$ hydroxamic acid ester, and a suitable protecting group.

2. The method of claim 1, wherein R is a C$_1$-C$_{20}$ alkyl, C$_1$-C$_{20}$ haloalkyl C$_2$-C$_{20}$ hydroxyalkyl, C$_2$-C$_{20}$ thioalkyl, C$_2$-C$_{20}$ aminoalkyl, C$_2$-C$_{20}$ alkoxyalkyl, C$_2$-C$_{20}$ alkylthioalkyl, C$_2$-C$_{20}$ alkylaminoalkyl, C$_2$-C$_{20}$ alkenyl, C$_2$-C$_{20}$ alkynyl, C$_2$-C$_{20}$ acyl, C$_6$-C$_{20}$ alkylaryl, C$_6$-C$_{20}$ arylalkyl, C$_6$-C$_{12}$ aryl, C$_2$-C$_{20}$ carboxylic acid ester, C$_1$-C$_{20}$ carboxylic acid amide, C$_3$-C$_{12}$ cycloalkyl, C$_1$-C$_{12}$ heteroaryl, or a C$_1$-C$_{12}$ heterocyclyl; and wherein said alkyl, haloalkyl, hydroxyalkyl, thioalkyl, aminoalkyl, alkoxyalkyl, alkylthioalkyl, alkylaminoalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, —OH, —CN, —NO$_2$, —SH, —OR, —SR, C$_1$-C$_6$ alkoxy, C$_1$-C$_8$ alkyl, C$_2$-C$_8$ alkenyl, C$_2$-C$_8$ alkynyl, C$_1$-C$_6$ aminoalkyl, C$_6$-C$_{20}$ aralkyl, C$_6$-C$_{12}$ aryl, C$_3$-C$_8$ cycloalkyl, C$_1$-C$_{12}$ heteroaryl, C$_1$-C$_{12}$ heterocyclyl, C$_2$-C$_{20}$ carboxylic acid ester, C$_3$-C$_{20}$ carboxylic acid amide, C$_1$-C$_6$ hydroxyalkyl, C$_2$-C$_3$ cyclic acetal, C$_1$-C$_{12}$ acetal, C$_1$-C$_{12}$ acyclic orthoester, C$_4$-C$_6$ cyclic orthoester, C$_1$-C$_{12}$ sulfone, C$_1$-C$_{12}$ sulfoxide, C$_2$-C$_{12}$ carbamate, C$_2$-C$_{12}$ urea, C$_2$-C$_{12}$ sulfonamide, C$_2$-C$_{12}$ sulfoxamide, C$_2$-C$_{12}$ phosphonate, C$_2$-C$_{12}$ phosphinoyl, and C$_2$-C$_{12}$ hydroxamic acid ester.

3. The method of claim 1, wherein R is chosen from a C$_1$-C$_{12}$ alkyl, C$_8$-C$_{12}$ arylalkyl, C$_6$-C$_{10}$ aryl, and C$_3$-C$_6$ cycloalkyl.

4. The method of claim 1, wherein R is chosen from a C$_2$-C$_{10}$ alkyl, benzyl, phenylethyl, phenyl, and cyclohexyl, and wherein ZnCl$_2$, ZnBr$_2$, or Zn(OMe)$_2$ is reacted with NaOMe so as to obtain an intermediate composition and then, said intermediate composition is reacted with at least one of RMgCl, RMgBr, and RMgI.

5. The method of claim 1, wherein said compound of formula (II) is reacted with said at least one compound chosen from compounds of formulas (IIIa), (IIIb), and (IIIc), in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof.

6. The method of claim 5, wherein said solvent is diethylether.

7. The method of claim 5, wherein said compound of formula (II) is reacted with said at least one compound chosen from compounds of formulas (IIIa), (IIIb), and (IIIc) by preparing a composition comprising said compound of formula (II) and said solvent, by adding said at least one compound chosen from compounds of formulas (IIIa), (IIIb), and (IIIc) to said composition so as to obtain a mixture, and by agitating said mixture.

8. The method of claim 5, wherein said compound of formula (II) is reacted with said at least one compound chosen from compounds of formulas (IIIa), (Mb), and (IIIc) by preparing a composition comprising said compound of formula (II) and said solvent, and by adding said at least one compound chosen from compounds of formulas (IIIa), (IIIb), and (IIIc) dissolved in said solvent to said composition so as to obtain a mixture, and by agitating said mixture.

9. The method of claim 1, wherein X is —OR$^1$ in which R$^1$ is a C$_1$-C$_{12}$ alkyl, C$_2$-C$_{12}$ haloalkyl, C$_3$-C$_{12}$ alkoxyalkyl, C$_4$-C$_{12}$ alkylaminoalkyl, or C$_2$-C$_{12}$ acyl.

10. The method of claim 9, wherein Zn(OR$^1$)$_2$ is reacted with at least one of RMgCl, RMgBr, and RMgI.

11. The method of claim 1, wherein Zn(OR$^1$)$_2$ is reacted with RMgCl in the presence of in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof.

12. The method of claim 10, wherein Zn(OR$^1$)$_2$ is chosen from Zn(OMe)$_2$, Zn(OAc)$_2$, Zn(OCH$_2$CH$_2$OCH$_3$)$_2$, and Zn(OCH$_2$CH$_2$OCH$_2$CH$_2$OCH$_3$)$_2$, Zn(OOCCH=CH$_2$)$_2$.

13. The method of claim 1, wherein ZnCl$_2$, or ZnBr$_2$ is reacted with at least one of RMgCl, RMgBr and RMgI, optionally in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof, so as to obtain an intermediate composition and then said compound of formula (VI) is reacted with said intermediate composition.

14. The method of claim 13, wherein R is chosen from a C$_2$-C$_{10}$ alkyl, benzyl, phenylethyl, phenyl, and cyclohexyl.

15. The method of claim 1, wherein $ZnCl_2$ is reacted with RMgCl so as to obtain an intermediate composition and then, NaOMe is reacted with the intermediate composition.

16. The method of claim 1, wherein R is chosen a $C_2$-$C_{20}$ alkenyl, $C_2$-$C_{20}$ alkynyl, $C_6$-$C_{20}$ alkylaryl, and $C_6$-$C_{12}$ aryl, X is —OMe, and wherein said compound of formula (II) and said at least one compound chosen from compounds of formulas (IIIa), (IIIb), and (IIIc) are reacted together in the presence of NaOMe.

17. A method for preparing a compound of formula (Ia):

$$R^2ZnR^3 \qquad \text{(Ia)}$$

wherein $R^2$ and $R^3$ are the same or different and they represent a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, said method comprising reacting a compound of formula (IIa) with a compound of formula (IIIg), and a compound of formula (VI):

$$R^2ZnX \qquad \text{(IIa)}$$

$$R^3M^1T \qquad \text{(IIIg)}$$

$$MOR^6 \qquad \text{(VI)}$$

wherein

X is chosen from —$OR^1$, —$SR^1$, Cl, Br, $C_2$-$C_{20}$ alkylcarboxylate, $C_2$-$C_{12}$ heteroarylcarboxylate, and $C_6$-$C_{20}$ arylcarboxylate;

$R^2$ and $R^3$ are as previously defined;

$M^1$ is Mg;

M is Na or K;

T is F, Cl, Br, I, $OSO_2R^2$, OR, CN, or $OC(O)R^2$;

$R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl; and $R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, said alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from a halogen atom, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group.

18. The method of claim 17, wherein said compound of formula (IIa) is reacted with said compound of formula (IIIg) so as to obtain an intermediate composition, and then said compound of formula (VI) is reacted with said intermediated composition, wherein $R^2$ and $R^3$ are the same or different and they represent a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl; and wherein said alkyl, haloalkyl, hydroxyalkyl, thioalkyl, aminoalkyl, alkoxyalkyl, alkylthioalkyl, alkylaminoalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from a halogen atom, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, and $C_2$-$C_{12}$ hydroxamic acid ester.

19. A method for preparing a compound of formula (IV):

$$Zn(OR^1)_2 \qquad \text{(IV)}$$

wherein $R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or said $R^1$ are linked together so as to form a 5 to 8 membered ring;

said alkyl, haloalkyl, hydroxyalkyl, thioalkyl, aminoalkyl, alkoxyalkyl, alkylthioalkyl, alkylaminoalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from a halogen atom, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group;

said method comprising reacting a compound of formula (II) with a compound of formula (V):

$$ZnX_2 \quad (II)$$

$$MOR^1 \quad (V)$$

wherein
X is Cl, or Br;
M is Na or K; and
$R^1$ is as previously defined,
in the presence of an organic solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof.

20. A method for preparing a substantially salt-free diorganozinc compound of formula (I) or a substantially salt-free composition comprising a diorganozinc compound of formula (I) and at least one solvent, said method comprising:

$$R_2Zn \quad (I)$$

wherein
R is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_4$-$C_{30}$ alkylsilylalkyl, $C_9$-$C_{30}$ (alkyl)(aryl)silylalkyl, $C_{19}$-$C_{30}$ arylsilylalkyl, $C_4$-$C_{30}$ (alkyl)(heteroaryl)silylalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl,
said method comprising:
reacting a composition comprising compound of formula (I) and a compound of formula (VII), with a compound of formula (VI), so as to obtain a mixture comprising a solid phase and a liquid phase or at least two solids;

$$MOR^6 \quad (VI)$$

$$M^1X_2 \quad (VII)$$

wherein
X is chosen from —$OR^1$, —$SR^1$, Cl, Br, I, $C_2$-$C_{20}$ alkylcarboxylate, $C_2$-$C_{12}$ heteroarylcarboxylate, and $C_6$-$C_{20}$ arylcarboxylate;
M is Na or K;
$M^1$ is Mg, Mn, Zr, Ti, or Ni;
$R^1$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl, or
said $R^1$ are linked together so as to form a 5 to 8 membered ring; and
$R^6$ is a $C_1$-$C_{20}$ alkyl, $C_1$-$C_{20}$ haloalkyl $C_2$-$C_{20}$ hydroxyalkyl, $C_2$-$C_{20}$ thioalkyl, $C_2$-$C_{20}$ aminoalkyl, $C_2$-$C_{20}$ alkoxyalkyl, $C_2$-$C_{20}$ alkylthioalkyl, $C_2$-$C_{20}$ alkylaminoalkyl, $C_2$-$C_{20}$ alkenyl, $C_2$-$C_{20}$ alkynyl, $C_2$-$C_{20}$ acyl, $C_6$-$C_{20}$ alkylaryl, $C_6$-$C_{20}$ arylalkyl, $C_6$-$C_{12}$ aryl, $C_2$-$C_{20}$ carboxylic acid ester, $C_1$-$C_{20}$ carboxylic acid amide, $C_3$-$C_{12}$ cycloalkyl, $C_1$-$C_{12}$ heteroaryl, or a $C_1$-$C_{12}$ heterocyclyl,
said alkyl, haloalkyl, hydroxyalkyl, thioalkyl, aminoalkyl, alkoxyalkyl, alkylthioalkyl, alkylaminoalkyl, alkylsilylalkyl, (alkyl)(aryl)silylalkyl, arylsilylalkyl, (alkyl)(heteroaryl)silylalkyl, alkenyl, alkynyl, alkylaryl, arylalkyl, aryl, acyl, carboxylic acid ester, carboxylic acid amide, cycloalkyl, heteroaryl, and heterocyclyl, being unsubstituted or substituted with at least one substituent chosen from F, Cl, Br, I, a deuterium atom, a tritium atom, —OH, —CN, —$NO_2$, —SH, —OR, —SR, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, $C_2$-$C_{20}$ carboxylic acid ester, $C_3$-$C_{20}$ carboxylic acid amide, $C_1$-$C_6$ hydroxyalkyl, $C_2$-$C_3$ cyclic acetal, $C_1$-$C_{12}$ acetal, $C_1$-$C_{12}$ acyclic orthoester, $C_4$-$C_6$ cyclic orthoester, $C_1$-$C_{12}$ sulfone, $C_1$-$C_{12}$ sulfoxide, $C_2$-$C_{12}$ carbamate, $C_2$-$C_{12}$ urea, $C_2$-$C_{12}$ sulfonamide, $C_2$-$C_{12}$ sulfoxamide, $C_2$-$C_{12}$ phosphonate, $C_2$-$C_{12}$ phosphinoyl, $C_2$-$C_{12}$ hydroxamic acid ester, and a suitable protecting group;
separating said solid phase and said liquid phase from one another or separating said at least two solids from one another.

21. The method of claim 11, wherein $Zn(OR^1)_2$ is chosen from $Zn(OMe)_2$, $Zn(OAc)_2$, $Zn(OCH_2CH_2OCH_3)_2$, and $Zn(OCH_2CH_2OCH_2CH_2OCH_3)_2$, $Zn(OOCCH=CH_2)$ and wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

22. The method of claim 21, wherein $Zn(OR^1)_2$ is chosen from $Zn(OMe)_2$ and $Zn(OAc)_2$.

23. The method of claim 1, wherein $Zn(OR^1)_2$ is reacted with RMgCl in the presence of diethylether.

24. The method of claim 1, wherein $Zn(OMe)_2$ is reacted with RMgCl in the presence of diethylether.

25. The method of claim 1, wherein wherein $Zn(OR^1)_2$ is reacted with at least one of RMgCl, RMgBr, and RMgI in the presence of in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof.

26. The method of claim 25, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

27. The method of claim 25, wherein said solvent is diethylether.

28. The method of claim 25, wherein $Zn(OR^1)_2$ is chosen from $Zn(OMe)_2$, $Zn(OAc)_2$, $Zn(OCH_2CH_2OCH_3)_2$, and $Zn(OCH_2CH_2OCH_2CH_2OCH_3)_2$, $Zn(OOCCH=CH_2)$.

29. The method of claim 28, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

30. The method of claim 13, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

31. The method of claim 30, wherein said compound of formula (VI) is NaOMe.

32. The method of claim 31, wherein R is chosen from a $C_1$-$C_{12}$ alkyl, $C_8$-$C_{12}$ arylalkyl, $C_6$-$C_{10}$ aryl, and $C_3$-$C_6$ cycloalkyl.

33. The method of claim 1, wherein $ZnCl_2$ or $ZnBr_2$ is reacted with at least one of RMgCl, RMgBr and RMgI, so as

34. The method of claim 33, wherein said compound of formula (VI) is NaOMe.

35. The method of claim 1, wherein $ZnCl_2$ is reacted with RMgCl in the presence of a solvent chosen from diethylether, t-butylmethylether, dibutylether, diphenylether, diisopropylether, dipropylether, dipentylether, dimethoxymethane, cyclopentylmethylether, diethoxymethane, and mixtures thereof, so as to obtain an intermediate composition and then, NaOMe is reacted with the intermediate composition.

36. The method of claim 35, wherein R is chosen from a $C_1$-$C_{12}$ alkyl, $C_8$-$C_{12}$ arylalkyl, $C_6$-$C_{10}$ aryl, and $C_3$-$C_6$ cycloalkyl.

37. the method of claim 36, wherein said solvent is diethylether.

38. The method of claim 1, wherein $ZnX_2$ is reacted with said compound of formula (VI) so as to obtain an intermediate composition and then, said intermediate composition is reacted with at least one of RMgCl, RMgBr, and RMgl.

39. The method of claim 1, wherein $ZnX_2$ is reacted with said compound of formula (VI) in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof, so as to obtain an intermediate composition and then, said intermediate composition is reacted with at least one of RMgCl, RMgBr, and RMgl.

40. The method of claim 39, wherein said compound of formula (VI) is NaOMe.

41. The method of claim 39, wherein $ZnX_2$ is $ZnCl_2$.

42. The method of claim 39, wherein $ZnX_2$ is $ZnBr_2$.

43. The method of claim 41, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

44. The method of claim 43, wherein said intermediate composition is reacted with RMgCl.

45. The method of claim 44, wherein R is chosen from a $C_1$-$C_{12}$ alkyl, $C_8$-$C_{12}$ arylalkyl, $C_6$-$C_{10}$ aryl, and $C_3$-$C_6$ cycloalkyl.

46. The method of claim 1, wherein $ZnCl_2$ or $ZnBr_2$ is reacted with NaOMe so as to obtain an intermediate composition and then, said intermediate composition is reacted with at least one of RMgCl, RMgBr, and RMgl.

47. The method of claim 1, wherein $ZnCl_2$ is reacted with NaOMe so as to obtain an intermediate composition and then, said intermediate composition is reacted with RMgCl.

48. The method of claim 41, wherein $ZnCl_2$ is reacted with NaOMe in the presence of a solvent chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof, so as to obtain said intermediate composition and then, said intermediate composition is reacted with with RMgCl.

49. The method of claim 48, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

50. the method of claim 48, wherein said solvent is diethylether.

51. The method of claim 49, wherein R is chosen from a $C_1$-$C_{12}$ alkyl, $C_8$-$C_{12}$ arylalkyl, $C_6$-$C_{10}$ aryl, and $C_3$-$C_6$ cycloalkyl.

52. The method of claim 21, wherein R is chosen from a $C_1$-$C_{12}$ alkyl, $C_8$-$C_{12}$ arylalkyl, $C_6$-$C_{10}$ aryl, and $C_3$-$C_6$ cycloalkyl.

53. The method of claim 25, wherein $Zn(OMe)_2$ is reacted with at least one of RMgCl and RMgBr.

54. The method of claim 26, wherein R is chosen from a $C_2$-$C_{10}$ alkyl, benzyl, phenylethyl, phenyl, and cyclohexyl.

55. The method of claim 54, wherein said solvent is diethylether.

56. The method of claim 18, wherein said compound of formula (IIa) is $R^2ZnCl$; said compound of formula (IIIg) is $R^3MgCl$ and said compound of formula (VI) is NaOMe.

57. The method of claim 18, wherein said compound of formula (IIa) is $R^2ZnOMe$; said compound of formula (IIIg) is $R^3MgCl$ and said compound of formula (VI) is NaOMe.

58. The method of claim 19, wherein said compound of formula (IV) is $Zn(OMe)_2$.

59. The method of claim 58, wherein said compound of formula (II) is $ZnCl_2$ and said compound of formula (V) is NaOMe.

60. The method of claim 59, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

61. The method of claim 59, wherein said solvent is diethylether.

62. The method of claim 58, wherein said compound of formula (II) is $ZnBr_2$ and said compound of formula (V) is NaOMe.

63. The method of claim 62, wherein said solvent is chosen from diethylether, t-butylmethylether, dibutylether, diphenylether, diisopropylether, dipropylether, dipentylether, dimethoxymethane, cyclopentylmethylether, diethoxymethane, and mixtures thereof.

64. The method of claim 62, wherein said solvent is diethylether.

65. The method of claim 20, wherein reacting said composition comprising said compound of formula (I) and said compound of formula (VII), with said compound of formula (VI) is carried out in the presence of a solvent so as to obtain said mixture comprising said solid phase and said liquid phase.

66. The method of claim 65, wherein said method further comprises substantially removing at least a portion of said solvent from said liquid phase.

67. The method of claim 65, wherein said method further comprises, after separating said solid phase and said liquid phase from one another, substantially removing at least a portion of said solvent from said liquid phase.

68. The method of claim 65, wherein said solvent is chosen from diethylether, t-butylmethylether, dibutylether, diphenylether, diisopropylether, dipropylether, dipentylether, dimethoxymethane, cyclopentylmethylether, diethoxymethane, a glyme-type solvent, analogues thereof, derivatives thereof, and mixtures thereof.

69. The method of claim 67, wherein said solvent is chosen from diethylether, t-butylmethylether, dibutylether, diphenylether, diisopropylether, dipropylether, dipentylether, dimethoxymethane, cyclopentylmethylether, diethoxymethane and mixtures thereof.

70. The method of claim 67, wherein said solvent is chosen from diethylether, tert-butylmethylether, 2-methyltetrahydrofuran and diethoxymethane.

71. The method of claim 20, wherein said compound of formula (VII) is $MgCl_2$, $MgBr_2$, or $MgI_2$, and in said compound of formula (VI) $R^6$ is a $C_1$-$C_4$ alkyl.

72. The method of claim 67, wherein said compound of formula (VII) is $MgCl_2$, $MgBr_2$, or $MgI_2$, and said compound of formula (VI) is NaOMe.

73. The method of claim 68, wherein said compound of formula (VII) is $MgCl_2$, $MgBr_2$, or $MgI_2$, and said compound of formula (VI) is NaOMe.

74. The method of claim 69, wherein said compound of formula (VII) is $MgCl_2$ and said compound of formula (VI) is NaOMe.

75. The method of claim 70, wherein said compound of formula (VII) is $MgCl_2$ and said compound of formula (VI) is NaOMe.

* * * * *